US010828329B2

(12) United States Patent
Laganière et al.

(10) Patent No.: US 10,828,329 B2
(45) Date of Patent: Nov. 10, 2020

(54) METHODS FOR CULTURING AND/OR DIFFERENTIATING HEMATOPOIETIC STEM CELLS INTO PROGENITORS AND USES THEREOF

(71) Applicant: HEMA-QUEBEC, Saint-Laurent (CA)

(72) Inventors: Josée Laganière, Quebec (CA); Nellie Dumont, Quebec (CA)

(73) Assignee: HEMA-QUEBEC, Saint-Laurent (CA)

( * ) Notice: Subject to any disclaimer, the term of this patent is extended or adjusted under 35 U.S.C. 154(b) by 212 days.

(21) Appl. No.: 15/579,489

(22) PCT Filed: Jun. 3, 2016

(86) PCT No.: PCT/CA2016/050630
§ 371 (c)(1),
(2) Date: Dec. 4, 2017

(87) PCT Pub. No.: WO2016/191879
PCT Pub. Date: Dec. 8, 2016

(65) Prior Publication Data
US 2018/0147239 A1 May 31, 2018

Related U.S. Application Data

(60) Provisional application No. 62/335,983, filed on May 13, 2016, provisional application No. 62/171,492, filed on Jun. 5, 2015.

(51) Int. Cl.
*A61K 35/15* (2015.01)
*A61K 35/28* (2015.01)
*A61K 35/19* (2015.01)
*C12N 5/078* (2010.01)
*C12N 5/0789* (2010.01)

(52) U.S. Cl.
CPC .............. *A61K 35/15* (2013.01); *A61K 35/19* (2013.01); *A61K 35/28* (2013.01); *C12N 5/0644* (2013.01); *C12N 5/0647* (2013.01); *A61K 2300/00* (2013.01); *C12N 2500/36* (2013.01); *C12N 2501/125* (2013.01); *C12N 2501/14* (2013.01); *C12N 2501/145* (2013.01); *C12N 2501/2306* (2013.01); *C12N 2501/2309* (2013.01); *C12N 2501/26* (2013.01); *C12N 2501/998* (2013.01); *C12N 2501/999* (2013.01); *C12N 2523/00* (2013.01)

(58) Field of Classification Search
CPC ....... A61K 35/15; A61K 35/19; C12N 5/0644
See application file for complete search history.

(56) References Cited

U.S. PATENT DOCUMENTS 7,452,662 B2   11/2008   Dupuis et al.

FOREIGN PATENT DOCUMENTS

| CA | 2562760 C | 11/2005 |
| EP | 1743024 B1 | 9/2011 |
| WO | WO2005103234 A1 | 11/2005 |
| WO | WO2013110198 A1 | 8/2013 |

OTHER PUBLICATIONS

Cortin et al., "Efficient in vitro megakaryocyte maturation using cytokine cocktails optimized by statistical experimental design"; Experimental Hematology; 2005, vol. 33, pp. 1182-1191.
Fares et al., "Pyrimidoindole derivatives are agonists of human hematopoietic stem cell self-renewal"; Science | AAAS; 2014, vol. 345, Issue 6203, pp. 1509-1512.
Ivetic et al., "Producing megakaryocytes from a human peripheral blood source"; Transfusion; 2016, vol. 56, pp. 1066-1074.
Majeti et al., "Identification of a hierarchy of multipotent hematopoietic progenitors in human cord blood"; Cell Stem Cell; 2007, vol. 1, pp. 635-645.
Pineault et al., "Characterization of the effects and potential mechanisms leading to increased megakaryocytic differentiation under mild hyperthermia"; Stem Cells and Development; 2008, vol. 17, pp. 483-493.
Proulx et al., "Increased megakaryopoiesis in cultures of CD34-enriched cord blood cells maintained at 39 degrees C"; Wiley Periodicals Inc.; 2004, vol. 88, No. 6, pp. 675-680.
Robert et al., "Glycoprotein Ibα receptor instability is associated with loss of quality in platelets produced in culture"; Stem Cells and Development; 2011, vol. 20, No. 3, pp. 379-390.
Tounkara et al., "Mild hyperthermia promotes and accelerates development and maturation of erythroid cells"; Cells Stem and Development; 2012, vol. 21, No. 17, pp. 3197-3208.
International Search Report and Writen Opinion for PCT/CA2016/050630, dated Aug. 22, 2016, 8 pages.
International Preliminary Report on Patentability for PCT/CA2016/050630, dated Dec. 5, 2017, 6 pages.

(Continued)

*Primary Examiner* — Teresa E Knight
(74) *Attorney, Agent, or Firm* — Greer, Burns & Crain, Ltd.

(57) ABSTRACT

The present description relates to in vitro methods for culturing hematopoietic stem cells (HSCs) under mild hyperthermia conditions (e.g., between 38° C. and 40° C.) in the presence of a pyrimidoindole derivative agonist of hematopoietic stem cell expansion. The combined use of mild hyperthermia and the pyrimidoindole derivative act synergistically to promote expansion of CD34+ HSCs and/or differentiation into progenitor cells (e.g., megakaryocytic progenitors). The present description also relates to in vitro expanded cell populations of HSCs and/or progenitors, as well as uses thereof in therapy (e.g., transplantation).

20 Claims, 23 Drawing Sheets

(56) References Cited

OTHER PUBLICATIONS

PCT/CA2016/050630, International Search Report, dated Aug. 22, 2016 (3 pages).
Pineault et al., "Characterization of the Effects and Potential Mechanisms Leading to Increased Megakaryocytic Differentiation under Mild Hyperthermia" Stem Cells and Development, 2008, v 17, p. 483-493.

METHODS FOR CULTURING AND/OR DIFFERENTIATING HEMATOPOIETIC STEM CELLS INTO PROGENITORS AND USES THEREOF

CROSS REFERENCE TO RELATED APPLICATIONS

This application is a U.S. National Stage under 35 U.S.C. § 371 of International Application No. PCT/CA2016/050630, filed Jun. 3, 2016, which claims priority to U.S. Provisional Patent application No. 62/171,492, filed Jun. 5, 2015, and U.S. Provisional Patent application No. 62/335,983, filed May 13, 2016.

The present description relates to hematopoietic stem cells. More particularly, the present description relates to culturing hematopoietic stem cells under mild hyperthermia (e.g., between 38° C. and 40° C.) and in the presence of a pyrimidoindole derivative agonist of hematopoietic stem cell expansion.

BACKGROUND

Hematopoietic stem cells (HSCs) are derived from the mesoderm and are responsible for the production of all cellular components found in blood, whether of the myeloid or lymphoid lineages. HSCs differentiate into common myeloid progenitors (CMPs) and common lymphoid progenitors (CLPs). CMPs give rise to cells of the erythroid, granulocytic, monocytic, megakaryocytic, and dendritic lineages, whereas CLPs lead to the derivation of T and B lymphocytes, plasma cells, natural killer cells and lymphoid dendritic cells. Terminal differentiation of myeloid lineage cells ultimately leads to the generation and renewal of red blood cells, granulocytes, monocytes, myeloid-derived dendritic cells, and platelets. Additionally, HSCs (primitive or long term) have the capacity for self-renewal, thereby ensuring an adequate supply of progenitors and terminally differentiated blood cells for the entire lifetime of an individual. The ability of these cells to self-renew has led to major advances in the medical field, namely, HSC transplantation as a treatment modality in patients suffering from hematological cancers or bone marrow failure. Historically, the bone marrow has been the primary source of HSCs, and remains to this day an important source of cells for bone marrow replacement. Since then, umbilical cord blood and peripheral blood from G-CSF-mobilized donors have also been used as HSC sources.

In parallel with their use in the clinic, HSCs have been the subject of intense research efforts aimed at the in vitro culture, expansion, differentiation into cells of various lineages, and the production of blood components in the laboratory. This research led to the discovery of several lineage-specific cytokines which nowadays are routinely used in various culture methods allowing the preferential growth and/or differentiation of hematopoietic stem cells towards specific lineages. Additionally, it was discovered that culturing HSCs under fever-like mild hyperthermia (39° C. instead of the standard temperature of 37° C.) leads to an accelerated expansion and differentiation towards the megakaryocytic lineage in the presence of a megakaryocyte-inducing cytokine cocktail (Proulx et al., 2004). More recently, a class of pyrimidoindole compounds was identified for its capacity to expand long-term hematopoietic stem cells (Fares et al, 2014).

Despite these advances, there are a number of shortcomings to the in vitro expansion of HSCs and their preferential differentiation towards specific myeloid lineages. For example, it is still particularly difficult to expand HSCs in vitro, while maintaining a primitive phenotype and controlled differentiation. Efficient expansion and maintenance of cells into a specific lineage also remain a challenge. For example, the levels of expansion required to envision the in vitro production of blood components remains insufficient with today's technology. In addition, current culture methods generally give rise to heterogeneous cellular populations that are not amenable to medical applications for specific clinical indications. The in vitro production of specific populations of stem cells and progenitors will require substantial improvements in order to enable their use in the clinic. There is thus a need for methods and technologies enabling massive in vitro expansion, while simultaneously allowing control of the direction and extent of differentiation of hematopoietic stem and progenitor cells into homogeneous cell populations for clinical use and mass production.

The present description refers to a number of documents, the content of which is herein incorporated by reference in their entirety.

SUMMARY

The present description arises from the surprising discovery that hematopoietic stem cells (HSCs) may be advantageously cultured under mild hyperthermia (e.g., between 38° C. and 40° C.) and in the presence of a pyrimidoindole derivative agonist of hematopoietic stem cell expansion. The combined use of mild hyperthermia and the pyrimidoindole derivative are shown herein to act synergistically to promote expansion of CD34+ HSCs (including long-term HSCs) and/or differentiation into "lineage-primed" or progenitor cells, and/or their maintenance (e.g., myeloid progenitors, megakaryocytic progenitors).

Indeed, in some embodiments, the combination of mild hyperthermia and a pyrimidoindole derivative agonist of hematopoietic stem cell expansion was shown to exponentially expand HSCs (CD34+ cells) when culture media favoring hematopoietic stem cell self-renewal were used. Without being bound by theory, the results disclosed herein suggest that mild hyperthermia combined with the use of a pyrimidoindole compound preserves the anti-differentiation effects of the pyrimidoindole compound, while simultaneously potentiating the stimulatory effects of the mild hyperthermia incubation temperature.

In other embodiments, the combination of mild hyperthermia and a pyrimidoindole derivative agonist of hematopoietic stem cell expansion was also shown to exponentially increase differentiation of HSCs into progenitor cells (e.g., myeloid progenitors, megakaryocytic progenitors), when culture conditions that favor differentiation towards the megakaryocytic lineage were used. Without being bound by theory, the results disclosed herein suggest that the pyrimidoindole compound blocks the hyperthermia-induced differentiation of HSCs before the mature megakaryocyte stage, and/or preferentially expands and maintains megakaryocytic progenitors. Thus, in some embodiments, the pyrimidoindole compound may be removed and the cells may be further propagated under conditions of mild hyperthermia, thereby producing a more synchronized cell population.

Accordingly, the present description may relate to the following aspects:

1. An in vitro method for culturing hematopoietic stem cells, said method comprising:
   (a) propagating said hematopoietic stem cells in a cell culture medium comprising a pyrimidoindole derivative agonist of hematopoietic stem cell expansion; and
   (b) incubating said hematopoietic stem cells at an incubation temperature between 38° C. and 40° C.
2. The method of aspect 1, wherein said hematopoietic stem cells are CD34+ hematopoietic stem cells.
3. The method of aspect 1 or 2, wherein said hematopoietic stem cells are from:
   (a) umbilical cord blood;
   (b) bone marrow;
   (c) peripheral blood;
   (d) induced pluripotent stem cells;
   (e) embryonic stem cells;
   (f) transdifferentiated from differentiated cells of non-hematopoietic origin;
   (g) genetically modified hematopoietic stem cells;
   (h) immortalized hematopoietic stem cells;
   (i) other sources of pluripotent or multipotent cells; or
   (j) any combination thereof.
4. The method of aspect 3, wherein said hematopoietic stem cells are from mobilized peripheral blood cells.
5. The method of aspect 3, wherein said hematopoietic stem cells are from unmobilized peripheral blood cells.
6. The method of aspect 4 or 5, wherein said hematopoietic stem cells are from residual cells following leukoreduction, deleukocytation, and/or other blood purification or processing of peripheral blood.
7. The method of any one of aspects 1 to 6, wherein said hematopoietic stem cells are incubated in a cell culture medium comprising a pyrimidoindole derivative agonist of hematopoietic stem cell expansion, and/or at an incubation temperature between 38° C. and 40° C., for at least 4, 5, 6, 7, 8, 9, 10, 11, 12, 13, 14, 15, 16, 17, 18, 19, 20, or 21 days.
8. The method of any one of aspects 1 to 7, wherein said incubation temperature is 39° C.
9. The method of any one of aspects 1 to 8, wherein said pyrimidoindole derivative agonist of hematopoietic stem cell expansion is:
   (a) a pyrimido[4,5-b]indole derivative;
   (b) (1r,4r)-N1-(2-benzyl-7-(2-methyl-2H-tetrazol-5-yl)-9H-pyrimido[4,5-b]indol-4-yl)cyclohexane-1,4-diamine;
   (c) methyl 4-(3-(piperidin-1-yl)propylamino)-9H-pyrimido[4,5-b]indole-7-carboxylate;
   (d) methyl 4-(3-(piperidin-1-yl)propylamino)-9H-pyrimido[4,5-b]indole-7-carboxylate hydrochloride;
   (e) a pharmaceutically acceptable salt, solvate, prodrug, or stereoisomer of any one of (a) to (d); or
   (f) any combination of (a) to (e).
10. The method of any one of aspects 1 to 9, wherein said cell culture medium comprises stem cell factor (SCF); thrombopoietin (TPO); or both SCF and TPO.
11. The method of any one of aspects 1 to 9, wherein said method is for expanding hematopoietic stem cells, and wherein said cell culture medium is a hematopoietic stem cell culture medium.
12. The method of aspect 11, wherein said hematopoietic stem cell culture medium comprises: human FMS-like tyrosine kinase 3 ligand (FLT3); stem cell factor (SCF); thrombopoietin (TPO); low-density lipoprotein (LDL); or any combination thereof.
13. The method of any one of aspects 1 to 9, wherein said method is for culturing hematopoietic stem cells to produce megakaryocytic progenitor cells, and wherein said cell culture medium is a medium promoting differentiation of hematopoietic stem cells towards the megakaryocytic lineage.
14. The method of aspect 13, wherein said medium promoting differentiation of hematopoietic stem cells towards the megakaryocytic lineage comprises: stem cell factor (SCF); thrombopoietin (TPO); human FMS-like tyrosine kinase 3 ligand (FLT3); IL-6; IL-9; or any combination thereof.
15. The method of any one of aspects 1 to 9, wherein said method is for culturing hematopoietic stem cells to produce myeloid progenitor cells, and wherein said cell culture medium is a medium promoting differentiation of hematopoietic stem cells towards the myeloid progenitor cell lineage.
16. The method of any one of aspects 1 to 15, further comprising: (c) removing said pyrimidoindole derivative agonist of hematopoietic stem cell expansion and continuing to propagate said cells at an incubation temperature between 38° C. and 40° C. or at an incubation temperature of about 37° C., thereby synchronizing said cells.
17. An in vitro expanded cell population which is:
   (a) a population of expanded hematopoietic stem cells produced by the method of aspect 11 or 12;
   (b) a population of megakaryocytic progenitor cells:
      (i) produced by the method of aspect 13 or 14; and/or
      (ii) comprising at least 40%, 45%, 50%, 55%, 60%, 65%, 70%, 75%, or 80% of CD34+/CD41+ cells;
   (c) a population of myeloid progenitor cells produced by the method of aspect 15;
   (d) a synchronized cell population produced by the method of aspect 16; or
   (e) any combination of (a) to (d).
18. The in vitro expanded cell population of aspect 17 for use in transplantation in a subject.
19. The in vitro expanded cell population of aspect 17, wherein:
   (a) said population of expanded hematopoietic stem cells is for use in hematopoietic stem cell transplantation, or for the manufacture of a therapeutic composition for same;
   (b) said population of megakaryocytic progenitor cells is for use in the treatment of thrombocytopenia, or for the manufacture of a therapeutic composition for same; or
   (c) said population of myeloid progenitor cells is for use in myeloid progenitor cell transplantation, or for the manufacture of a therapeutic composition for same.
20. Use of:
   (a) the population of expanded hematopoietic stem cells of aspect 17 for hematopoietic stem cell transplantation;
   (b) the population of megakaryocytic progenitor cells of aspect 17 for the treatment of thrombocytopenia; or
   (c) the population of myeloid progenitor cells of aspect 17 for myeloid progenitor cell transplantation.
21. A pharmaceutical composition comprising:
   (a) the population of expanded hematopoietic stem cells of aspect 17;
   (b) the population of megakaryocytic progenitor cells of aspect 17; or
   (c) the population of myeloid progenitor cells of aspect 17.

General Definitions

Headings, and other identifiers, e.g., (a), (b), (i), (ii), etc., are presented merely for ease of reading the specification and claims. The use of headings or other identifiers in the specification or claims does not necessarily require the steps or elements be performed in alphabetical or numerical order or the order in which they are presented.

The use of the word "a" or "an" when used in conjunction with the term "comprising" in the claims and/or the specification may mean "one" but it is also consistent with the meaning of "one or more", "at least one", and "one or more than one".

The term "about" is used to indicate that a value includes the standard deviation of error for the device or method being employed to determine the value. In general, the terminology "about" is meant to designate a possible variation of up to 10%. Therefore, a variation of 1, 2, 3, 4, 5, 6, 7, 8, 9 and 10% of a value is included in the term "about". Unless indicated otherwise, use of the term "about" before a range applies to both ends of the range.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps.

Other objects, advantages and features of the present description will become more apparent upon reading of the following non-restrictive description of specific embodiments thereof, given by way of example only with reference to the accompanying drawings.

BRIEF DESCRIPTION OF THE DRAWINGS

In the appended drawings:

FIG. 18C shows the fold-expansion of CB CD34+/CD45RA− cells (long-term hematopoietic stem cells; LT-HSC) cultured in StemSpan™ SFEM medium supplemented with the BS1 cytokine cocktail under mild hyperthermia and in the presence ("39") or absence ("CTL") of PIC.

DETAILED DESCRIPTION

Figure 1:
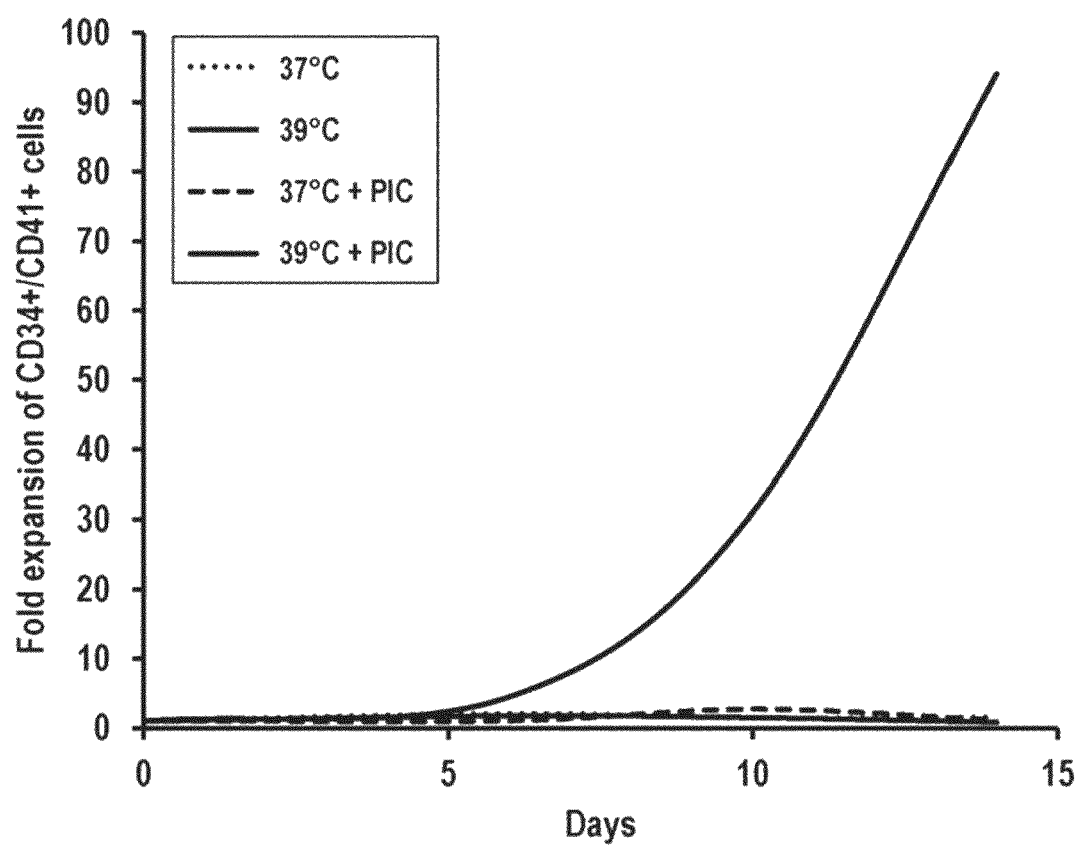
FIG. 1 shows the fold expansion of CD34+/CD41+ megakaryocytic progenitor cells as a function of time for CD34+ cells cultured under conditions that promote differentiation towards the megakaryocytic lineage. Four conditions were tested: (1) "37° C.": at standard temperature in the absence of a pyrimidoindole derivative agonist of hematopoietic stem cell expansion (PIC); (2) "37° C.+PIC": at standard temperature in the presence of 35 nM PIC; (3) "39° C.": under mild hyperthermia in the absence of PIC; or (4) "39° C.+PIC": under mild hyperthermia in the presence of 35 nM PIC.

The present description arises from the surprising discovery that cell culture conditions comprising mild hyperthermia (e.g., between 38° C. and 40° C.) and the presence of a pyrimidoindole derivative agonist of hematopoietic stem cell expansion, act synergistically to promote expansion of hematopoietic stem cells (HSGs) and/or differentiation into progenitor cells (e.g., myeloid progenitors, megakaryocytic progenitors). Indeed, in some embodiments, the combination of mild hyperthermia and of a pyrimidoindole derivative agonist of hematopoietic stem cell expansion was shown to exponentially expand hematopoietic stem cells. In addition, this combination was also shown, in some embodiments, to exponentially increase differentiation of HSGs into progenitor cells (e.g., myeloid progenitors, megakaryocytic progenitors).

In some aspects, the present description relates to an in vitro method for culturing hematopoietic stem cells, the method comprising: (a) propagating said hematopoietic stem cells in a cell culture medium comprising a pyrimidoindole derivative agonist of hematopoietic stem cell expansion; and (b) incubating said hematopoietic stem cells under conditions of mild hyperthermia (e.g., at an incubation temperature between 38° C. and 40° C.). In some embodiments, the method may further comprise: (c) removing the pyrimidoindole derivative agonist of hematopoietic stem cell expansion and continuing to propagate the cells at an incubation temperature between 38° C. and 40° C., thereby producing a more synchronized cell population.

As used herein, "hematopoietic stem cells" or "HSCs" refers to cells possessing both multipotency (i.e., can produce all cellular components found in blood, such as leukocytes, erythrocytes, platelets, etc.), and the ability to self-renew. The use of CD34 as a positive selection marker allows to enrich for hematopoietic stem cells, and thus, in some embodiments, CD34+ cells may be used as hematopoietic stem cells. In addition to CD34, a plurality of other hematopoietic stem cell markers can be used alone or in combination, to identify, enrich and/or isolate a given population of HSCs by methods known in the art (e.g., FACS, immunomagnetic particles). Examples of other markers that may be useful for this purpose include CD133/AC133+, Lin−, ALDH$^{hi}$ or ALDH$^{Bright}$, CD38−, CD71−, HLA-DR−, CD33−, CD117/c-kit+, CD59+, CD90/Thy-1+, and CD49f+. In particular, in some embodiments, long-term hematopoietic stem cells (LT-HSCs) may be identified, enriched and/or isolated using markers such as CD34+/ CD45RA−, CD34+/CD38−/CD45RA−, and CD49f+. Other markers not listed here may also be useful for identifying, enriching and/or isolating a given population of HSCs, and such markers are also considered within the scope of the present description. In some embodiments, the HSCs may be isolated or derived from cells of umbilical cord blood; bone marrow; peripheral blood; induced pluripotent stem cells; embryonic stem cells; cells obtained by transdifferentiation of non-hematopoietic, differentiated cells; HSCs that have been genetically modified; HSCs that have been immortalized or engineered; other sources of pluripotent or multipotent cells; or any combination thereof. In some embodiments, the HSCs may be isolated or derived from mobilized peripheral blood cells (e.g. mobilized with G-CSF). In some embodiments, the HSCs may be isolated or derived from unmobilized peripheral blood cells (i.e., peripheral blood cells that have not been mobilized with, for example, G-CSF). In some embodiments, the HSCs may be isolated or derived from cells remaining after the leukoreduction and/or deleukocyration of mobilized or unmobilized peripheral blood cells (e.g., cells remaining in the leukoreduction chamber of a plateletpheresis apparatus, or cells recovered from leukoreduction filters of whole blood collection sets; these leukoreduction devices are otherwise discarded). It should be understood that the present description may be applied to HSCs from diverse sources and methods of purification, treatment, and/or concentration. Non limiting examples of such sources and methods are described herein, but other sources of HSCs not explicitly mentioned herein may also be used in accordance with the present description.

As used herein, the term "propagating" refers to the in vitro culture of cells (e.g., hematopoietic stem cells) to achieve a particular purpose, such as expanding a certain cell population (e.g., HSCs and/or CD34+ cells), and/or promoting cell differentiation towards a desired cell lineage (e.g., megakaryocytic lineage, or other lineages arising from myeloid progenitor cells). In some embodiments, "propagating" may refer to small "lab-scale" cell cultures or larger-scale cell cultures (e.g., using bioreactors). In some embodiments, the composition of the cell culture medium used for propagating the cells may be selected to promote expansion of a particular cell type (e.g., HSCs and/or CD34+ cells), or to promote differentiation towards a desired cell lineage (e.g., megakaryocytic lineage, or other lineages arising from myeloid progenitor cells). In some embodiments, the cell culture medium of the present description may comprise one or more cytokines. In some embodiments, the cytokines may comprise: stem cell factor (SCF); thrombopoietin (TPO); or both. As used herein, the expression "promote differentiation towards" refers to the general direction of cellular differentiation towards a particular endpoint, but not necessarily to the reaching of the endpoint (i.e., final differentiation of a cell into a mature, fully differentiated cell). Such media and additives (e.g., different cytokine cocktails and/or other cell culture media components to influence expansion and/or differentiation towards particular lineages) are generally known to the person skilled in the art. Many of the suitable media and additives are commercially available to the skilled person.

For example, for CD34+ cell culture and expansion with limited differentiation in the context of the present description, cells may be propagated in a variety of commercially available media such as StemSpan™ ACF, SFEM, or SFEM II, and supplemented with a commercially available cytokine cocktail such as CC110 (STEMCELL Technologies, Vancouver, BC, Canada). In some embodiments, a home-made (HM) cytokine cocktail may be prepared which may comprise: human FMS-like tyrosine kinase 3 ligand (FLT3) (e.g., 100 ng/mL), stem cell factor (SCF) (e.g., 100 ng/mL), thrombopoietin (TPO) (e.g., 50 ng/mL), low-density lipoprotein (LDL) (e.g., 10 µg/mL), or any combination thereof. Such cell culture media/cytokine cocktails and others, which enable the propagation of HSCs (e.g., CD34+ cells) under self-renewal conditions in the context of the present description, are herein referred to as "hematopoietic stem cell culture medium". However, other types of cell culture media and/or additives (e.g., cytokine cocktails) may be used and the present description should not be limited to the cell culture media employed in the present Examples.

For culture and differentiation towards the megakaryocytic lineage in the context of the present description, purified CD34+ cells may be cultured in a medium such as StemSpan™ ACF or SFEM medium (STEMCELL™ Technologies), supplemented with a cytokine cocktail such as the OMPC cytokine cocktail described in Robert et al., 2011, or the BS1 megakaryocyte expansion and differentiation cytokine cocktail described in Cortin et al., 2005. The OMPC cytokine cocktail includes TPO (e.g., 35 ng/mL), SCF (e.g., 10 ng/mL), and human FLT3 (11 ng/mL). The BS1 cytokine cocktail includes TPO (e.g., 30 ng/mL TPO), SCF (1 ng/mL), IL-6 (e.g., 7.5 ng/mL), and IL-9 (e.g., 13.5 ng/mL). Such cell culture media/cytokine cocktails and others, which promote the differentiation of HSCs towards the megakaryocytic lineage in the context of the present description, are herein referred to as "medium promoting differentiation of hematopoietic stem cells towards the megakaryocytic lineage". However, other types of cell culture media and/or additives (e.g., cytokine cocktails) may be used and the present description should not be limited to the cell culture media employed in the present Examples.

In some embodiments, different cell expansion methods or cell populations described herein may be used together for greater efficacy (e.g., to produce a cell population to be infused or transplanted in a subject to promote accelerated platelet recovery, for example).

In some embodiments, the cells may be propagated for at least 4, 5, 6, 7, 8, 9, 10, 11, 12, 13, 14, 15, 16, 17, 18, 19, 20, or 21 days. In some embodiments, the methods of the present description enable propagation of hematopoietic stem cells for at least 4, 5, 6, 7, 8, 9, 10, 11, 12, 13, 14, 15, 16, 17, 18, 19, 20, or 21 days, without appreciably losing cell viability and/or "stemness". As used herein, the expression "appreciably losing cell viability" refers to where the rate of cell death is greater than the rate of cell expansion, such that a net expansion of total viable cells of interest is no longer observed. The person of skill in the art will recognize that the cell culture medium may be adapted to suit particular needs of expansion and/or differentiation. In some embodiments, the cell culture medium may be a non-differentiating medium.

In some embodiments, mild hyperthermia and addition of a pyrimidoindole derivative agonist of hematopoietic stem cell expansion may be combined at different points in time and/or for variable lengths of time (e.g., simultaneously and/or in alternate fashion during a given in vitro culture period), depending on the desired outcome of the culture. Such variations are within the scope of some embodiments of the present description, wherein the variations result in an improved amount of cell expansion relative to the culture of HSCs using only mild hyperthermia or a pyrimidoindole derivative agonist of hematopoietic stem cell expansion for a given in vitro culture period.

Accordingly, in some embodiments, the present description relates to a method for expanding hematopoietic stem cells, and wherein said cell culture medium is a hematopoietic stem cell culture medium. In some embodiments, the methods for expanding hematopoietic stem cells in vitro may be useful for expanding HSCs from cord blood in order to reach a sufficient number of cells for successful engraftment in adults. In some embodiments, the present description relates to an in vitro method for expanding hematopoietic stem cells, the method comprising: (a) propagating said hematopoietic stem cells in a hematopoietic stem cell culture medium comprising a pyrimidoindole derivative agonist of hematopoietic stem cell expansion; and (b) incubating said hematopoietic stem cells at an incubation temperature between 38° C. and 40° C., wherein the level of hematopoietic stem cell expansion obtained is higher than that obtainable by culturing said hematopoietic stem cells in either (a) or (b) alone. In some embodiments, HSCs are expanded at least 20, 30, 40, 50, 60, 70, 80, 90, 100, 200, 300, 400, 500, 600, 700, 800, 900, or 1000-fold (e.g., between 5 and 21 days in culture). In some embodiments, the HSCs are long-term-repopulating HSCs (LT-HSCs), such as CD34+/CD45RA– cells, CD34+/CD38–/CD45RA– or CD49f+ cells. In some embodiments, the LT-HSCs are expanded at least 2, 5, 10, 15, 20, 30, 40, 50, 60, 70, 80, 90, 100, or 200-fold (e.g., between 5 and 21 days in culture). The skilled person will understand that the actual values of fold expansion obtained may vary depending on a number of factors, such as the quality and/or quantity of the starting material cells. These variations are within the scope of the present description.

In some embodiments, the present description relates to a method for culturing hematopoietic stem cells to produce myeloid progenitors, and wherein said cell culture medium is a medium promoting differentiation of hematopoietic stem cells towards myeloid progenitors. As used herein, "myeloid progenitor" refers to a hematopoietic cell that is capable of being induced to differentiate into one or more megakaryocytes, one or more erythrocytes, one or more mast cells or one or more myeloblasts. In some embodiments, myeloid progenitors may be identified as CD34+/CD41+ cells (megakaryocyte progenitors). In some embodiments, the present description relates to an in vitro method for culturing hematopoietic stem cells to produce myeloid progenitors, the method comprising: (a) propagating said hematopoietic stem cells in a cell culture medium promoting differentiation of hematopoietic stem cells towards myeloid progenitors, said cell culture medium comprising a pyrimidoindole derivative agonist of hematopoietic stem cell expansion; and (b) incubating said hematopoietic stem cells at an incubation temperature between 38° C. and 40° C., wherein the level of myeloid progenitors obtained is higher than that obtainable by culturing said hematopoietic stem cells in either (a) or (b) alone. In some embodiments, the myeloid progenitors may be promoted to differentiate into megakaryocytes. In some embodiments, myeloid progenitors are expanded at least 20, 30, 40, 50, 60, 70, 80, 90, 100, 200, 300, 400, 500, 600, 700, 800, 900, or 1000-fold (e.g., between 5 and 21 days in culture). The skilled person will understand that the actual values of fold expansion obtained may vary depending on a number of factors, such as the quality and/or quantity of the starting material cells. These variations are within the scope of the present description.

In some embodiments, the present description relates to a method for culturing hematopoietic stem cells to produce megakaryocytic progenitor cells, and wherein said cell culture medium is a medium promoting differentiation of hematopoietic stem cells towards the megakaryocytic lineage. As used herein, "megakaryocytic progenitor" refers to a hematopoietic cell that is capable of being induced to differentiate into one or more megakaryocytes. In some embodiments, the present description relates to an in vitro method for culturing hematopoietic stem cells to produce megakaryocytic progenitor cells, the method comprising: (a) propagating said hematopoietic stem cells in a cell culture medium promoting differentiation of hematopoietic stem cells towards the megakaryocytic lineage, said cell culture medium comprising a pyrimidoindole derivative agonist of hematopoietic stem cell expansion; and (b) incubating said hematopoietic stem cells at an incubation temperature between 38° C. and 40° C., wherein the level of megakaryocytic progenitor cells obtained is higher than that obtainable by culturing said hematopoietic stem cells in either (a) or (b) alone. In some embodiments, the megakaryocytic progenitors may be promoted to differentiate into platelets or platelet-like fragments. In some embodiments, megakaryocytic progenitors are expanded at least 20, 30, 40, 50, 60, 70, 80, 90, or 100-fold (e.g., between 5 and 14 days in culture). The skilled person will understand that the actual values of fold expansion obtained may vary depending on a number of factors, such as the quality and/or quantity of the starting material cells. These variations are within the scope of the present description.

In some aspects, the present description relates to the propagation of cells in the presence of a "pyrimidoindole derivative agonist of hematopoietic stem cell expansion". As used herein, this expression refers to small-molecule compounds sharing a degree of structural similarity with pyrimidoindole that have the ability to stimulate HSC expansion. It is understood that by "pyrimidoindole derivative agonist of hematopoietic stem cell expansion", a sufficient concentration or dose of the compound is present in the cell culture medium to elicit the desired effect (e.g., stimulate HSC expansion and/or synergize with the use of mild hyperthermia in the context of the present description). In some embodiments, the pyrimidoindole derivative may be a "pyrimido[4,5-b]indole derivative". Such derivatives have been previously described for example in WO 1993/020078; WO 1995/019970; WO 1997/002266; WO 1998/042708; WO 2000/066585; WO 2003/037898; WO 2004/058764; WO 2005/037825; WO 2006/116733; WO 2008/055233; WO 2009/004329, and WO 2010/006032. In some embodiments, the pyrimido[4,5-b]indole derivative may be a compound described for example in Fares et al., 2014, or WO 2013/110198, such as (1r,4r)-N1-(2-benzyl-7-(2-methyl-2H-tetrazol-5-yl)-9H-pyrimido[4,5-b]indol-4-yl)cyclohexane-1,4-diamine [UM171], or methyl 4-(3-(piperidin-1-yl)propylamino)-9H-pyrimido[4,5-b]indole-7-carboxylate [UM729]. Such compounds were shown to stimulate expansion of CD34+/CD45RA− mobilized peripheral blood cells, which are enriched in long-term-repopulating HSCs (LT-HSCs), without acting as suppressors of the aryl hydrocarbon receptor (AhR) pathway (Fares et al., 2014). Accordingly, in some embodiments, the pyrimidoindole derivative may include an AhR pathway-independent pyrimido[4,5-b]indole derivative agonist of CD34+/CD45RA− cell expansion. In some embodiments, the concentration the pyrimidoindole derivative agonist of hematopoietic stem cell expansion may be prepared as a stock solution in a carrier such as DMSO. In some embodiments, the concentration of the pyrimidoindole derivative agonist of hematopoietic stem cell expansion may be from 10, 15, 20, 25, or 30 nM, to 50, 60, 70, 80, 90, 100, 150, 200, 250, 300, 350, 400, 450, 500, 600, 700, 800, 900 or 1000 nM. The concentration of the pyrimidoindole derivative agonist of hematopoietic stem cell expansion may be modified based on the potency of the molecule, and other concentrations, not explicitly recited here, are also within the scope of the present description. In some embodiments, pharmaceutically acceptable salts, solvates, prodrugs, or stereoisomers of any of the above-mentioned pyrimidoindole derivatives may also be within the scope of the present description. As used herein, the term "prodrug" refers to a compound which, when metabolized (e.g., in vivo), yields the desired active compound. Typically, the prodrug is inactive, or less active than the desired active compound, but may provide advantageous handling, administration, or metabolic properties. Unless otherwise specified, a reference to a particular compound also includes prodrugs thereof.

In some embodiments, the pyrimidoindole derivatives of the present description may be used in combination with other compounds, such as an antagonist of aryl hydrocarbon receptor (AhR) (e.g., SR1: 4-[2-[[2-benzo[b]thien-3-yl-9-(1-methylethyl)-9H-purin-6-yl]amino]ethyl]-phenol). In some embodiments, the antagonist of aryl hydrocarbon receptor compound (e.g., SR1) may be prepared as a stock solution in a carrier such as DMSO. In some embodiments, the antagonist of aryl hydrocarbon receptor compound (e.g., SR1) may be used for example at between 100 and 1000 nM, between 200 and 900 nM, between 300 and 800 nM, between 400 and 800 nM, between 450 and 750 nM, between 700 and 800 nM, or between 450 and 550 nM.

In some aspects, the present description relates to the propagation of cells under mild hyperthermia. In some embodiments, "mild hyperthermia" refers to propagating cells at an incubation temperature between 38° C. and 40° C., preferably 39° C. Of course, the skilled person would understand that some transient variations outside the aforementioned temperature range may be permitted, as long as the cells are generally cultured/propagated at temperatures 1-3° C. higher than the recommended temperature for the given cell population (e.g., generally 37° C.). In some embodiments, the cells are maintained under mild hyperthermia for at least 4, 5, 6, 7, 8, 9, 10, 11, 12, 13, 14, 15, 16, 17, 18, 19, 20, or 21 days. In some embodiments, the cells are maintained under mild hyperthermia for at least 4, 5, 6, 7, 8, 9, 10, 11, 12, 13, 14, 15, 16, 17, 18, 19, 20, or 21 consecutive days.

In some aspects, the present description relates to an in vitro expanded cell population which is a population of expanded hematopoietic stem cells, myeloid progenitor cells, megakaryocytic progenitor cells, or any combination thereof produced by a method defined herein. In some embodiments, different in vitro expanded cell populations of the present description may be combined for greater therapeutic benefit (e.g., to promote accelerated platelet recovery).

In some embodiments, the in vitro expanded cell population of the present description may comprise at least 40%, 45%, 50%, 55%, 60%, 65%, 70%, 75%, or 80% of CD34+/CD41+ cells.

In some aspects, the present description relates to the use of an in vitro expanded cell population described herein for transplanting into a subject, or for the manufacture of a therapeutic composition for transplanting into a subject. In some embodiments, the in vitro expanded cell population may be a population of expanded hematopoietic stem cells for use in hematopoietic stem cell transplantation, or for the manufacture of a therapeutic composition for same. In some embodiments, the in vitro expanded cell population may be a population of megakaryocytic progenitor cells for use in the treatment of thrombocytopenia, or for the manufacture of a therapeutic composition for same. Accordingly, in some aspects, the present description relates to a pharmaceutical composition comprising: the population of expanded hematopoietic stem cells, myeloid progenitor cells, or megakaryocytic progenitor cells, as defined herein.

In some embodiments, the pharmaceutical composition may comprise a pharmaceutically acceptable carrier, such as normal buffered saline (e.g., about 135-150 mM NaCl). Other suitable carriers include, but are not limited to, water, buffered water, 0.4% saline, 0.3% glycine, and the like. Additional carriers suitable for use in delivering the cultured stem cells of the present invention are described in, e.g., REMINGTON'S PHARMACEUTICAL SCIENCES, Mack Publishing Co., Philadelphia, Pa., 18th ed. (1995).

Other objects, advantages and features of the present description will become more apparent upon reading of the following non-restrictive description of specific embodiments thereof, given by way of example only with reference to the accompanying drawings.

EXAMPLES

Example 1

Materials and Methods for Examples 2-5

1.1 Materials
All chemicals were purchased from Sigma-Aldrich (Oakville, ON, Canada), unless otherwise noted.
1.2 Isolation and Culture of CD34+ Cells from Human Umbilical Cord Blood
CD34+ cells were isolated from human umbilical cord blood by positive selection according to standard procedures. Purified CD34+ cells from either single units or pooled from several units of cord blood were seeded in 1 mL of the appropriate culture medium in 24-well plates at a density of approximately $10^5$ cells/mL. Cells were maintained at a density of $10^5$-$10^6$ cells/mL throughout the culture by dilution and/or medium replacement.

For culture and differentiation towards the megakaryocytic lineage, purified CD34+ cells were cultured in StemSpan™ ACF medium (STEMCELL™ Technologies, Vancouver, BC, Canada) supplemented with antibiotics and the "BS1" cytokine cocktail described previously (Cortin et al, 2005), and cell counts were performed on days 6, 10, and 14.

For CD34+ cell culture and expansion while limiting differentiation, cells were grown in StemSpan™-ACF medium (STEMCELL™ Technologies) supplemented with StemSpan™ CC110 cytokine cocktail (STEMCELL™ Technologies), and counted on days 4, 7, 10, 14, 17, and 21.

Cell counts and viability were measured using the NucleoCounter® NC250™ Viability and Cell Count Assay system (ChemoMetec Inc., Davis, Calif.), according to the manufacturer's instructions.
1.3 Cell Phenotype Analyses
Cell phenotypes were determined by flow cytometry on the indicated days using the following panel of labeled primary antibodies: CD34-FITC, CD45RA-APC, CD41a-APC, CD42b-PE, and CD235-PE.
1.4 CFU-MK Assay
Aliquots of cells grown in StemSpan™ ACF+BS1 culture medium were collected on the indicated days, and CFU-MK were determined using the Megacult™ C kit from STEMCELL™ Technologies, according to the manufacturer's instructions.

Example 2

Combination of Culture Under Mild Hyperthermia and Pyrimidoindole Compound PIC Increases Expansion of Megakaryocytic Progenitor Cells CD34+ cells were isolated and cultured for differentiation towards the megakaryocytic lineage as generally described in Example 1.2. To determine the effects of the combination of mild hyperthermia and a pyrimidoindole compound on megakaryocytic progenitor (MKP) cell expansion, the CD34+ cells were cultured at either 37° C. or 39° C., and in the presence of cell culture medium supplemented or not with 35 nM (final concentration) of the pyrimidoindole compound: (1r,4r)-N1-(2-benzyl-7-(2-methyl-2H-tetrazol-5-yl)-9H-pyrimido[4,5-b]indol-4-yl)cyclohexane-1,4-diamine hydrochloride ("UM171") herein referred to as "PIC". Flow cytometry was used to monitor the expansion of CD34+/CD41+ MKP cells over time, as described in Example 1.3.

As shown in FIG. 1, cells cultured at 37° C. in the presence ("37° C.+PIC") or absence ("37° C.") of PIC had less than 5-fold expansion of CD34+/CD41+ MKP cells, as did cells cultured under mild hyperthermia in the absence of PIC ("39° C."). Interestingly and surprisingly, the combination of mild hyperthermia and PIC ("39° C.+PIC") resulted in an expansion of CD34+/CD41+ MKP cells that reached nearly 100-fold by day 14, with a purity of CD34+/CD41+ cells generally above 40% (data not shown). These results show a potent synergistic effect of mild hyperthermia combined with a pyrimidoindole compound in stimulating expansion of MKP cells from CD34+ cells.

Example 3

Combination of Culture Under Mild Hyperthermia and Pyrimidoindole Compound PIC Yields a More Homogeneous Population of Megakaryocytic Progenitor Cells More thorough cell phenotypic profiles of the CD34+ cells isolated and cultured in Example 2 were determined on days 6, 10 and 14 by flow cytometry as described in Example 1.3. The results are summarized in Table 1, which shows the percentage of cells bearing the indicated cell surface marker or combination of markers.

TABLE 1

Phenotypic analysis of CD34+ cells cultured in conditions favoring MKP cell expansion

| | | Percentage of cells bearing cell surface marker(s) | | | | | | | |
|---|---|---|---|---|---|---|---|---|---|
| Day of culture | Conditions | CD34+ | CD34+/ CD41− | CD41+ | CD42+ | CD45RA+ | CD235+ | CD34+/ CD41+ | CD41+/ CD42+ |
| Day 6 | 37° C. | 80.82 | 47.29 | 42.50 | 15.41 | 71.94 | 19.75 | 31.21 | 15.13 |
| | 37° C. + PIC | 98.38 | 68.55 | 29.27 | 2.48 | 71.55 | 11.67 | 29.54 | 1.71 |
| | 39° C. | 27.93 | 8.89 | 72.30 | 34.93 | 62.37 | 35.89 | 34.93 | 34.84 |
| | 39° C. + PIC | 97.19 | 48.02 | 49.84 | 8.31 | 58.97 | 19.51 | 48.85 | 7.95 |
| Day 10 | 37° C. | 29.11 | 15.92 | 61.10 | 39.22 | 35.09 | 15.86 | 13.26 | 39.05 |
| | 37° C. + PIC | 84.39 | 64.40 | 24.84 | 2.55 | 76.43 | 7.45 | 20.21 | 1.30 |
| | 39° C. | 16.84 | 5.44 | 89.13 | 74.36 | 15.57 | 15.64 | 15.17 | 74.07 |
| | 39° C. + PIC | 87.29 | 21.37 | 73.31 | 17.30 | 46.94 | 14.40 | 67.10 | 17.09 |
| Day 14 | 37° C. | 21.41 | 4.44 | 81.52 | 44.49 | 34.55 | 18.53 | 14.49 | 44.41 |
| | 37° C. + PIC | 69.53 | 54.97 | 23.65 | 3.02 | 61.90 | 2.90 | 11.01 | 0.68 |
| | 39° C. | 13.8 | 2.48 | 88.23 | 69.6 | 27.68 | 36.8 | 10.1 | 68.05 |
| | 39° C. + PIC | 88.56 | 10.25 | 87.90 | 27.09 | 27.09 | 12.61 | 76.46 | 27.04 |

As shown in Table 1, culturing CD34+ cells under mild hyperthermia and in the presence of PIC ("39° C.+PIC") resulted in a greater proportion of CD34+/CD41+ MKP cells on days 6, 10 and 14, than culturing CD34+ cells at a standard temperature in the absence ("37° C.") or presence ("37° C.+PIC") of PIC, or than culturing the cells under mild hyperthermia without PIC ("39° C."). More particularly, CD34+ cells cultured for 14 days under mild hyperthermia and in the presence of PIC ("39° C.+PIC") yielded 76.5% of CD34+/CD41+ MKP cells, whereas the use of PIC alone ("37° C.+PIC") or mild hyperthermia alone ("39° C.") yielded only 11% and 10% of CD34+/CD41+ MKP cells, respectively. These results show that a more homogeneous cellular population of megakaryocytic progenitors can be obtained by culturing CD34+ hematopoietic stem cells in standard conditions favoring differentiation into megakaryocytic progenitors, wherein the standard culture conditions are modified by the combination of a pyrimidoindole compound and an incubation temperature of 39° C.

Furthermore, as shown in Table 1, cultures grown at 39° C. in the presence of PIC ("39° C.+PIC") only have 27% of cells of phenotype CD41+/CD42+ typical of mature megakaryocytes on day 14, whereas cultures grown at 39° C. in the absence of PIC ("39° C.") have 68% of CD41+/CD42+ mature megakaryocytes. Cultures grown at 37° C. in the presence of PIC ("37° C.+PIC") have virtually no CD41+/CD42+ mature megakaryocytes on day 14, whereas cultures grown at 37° C. in the absence of PIC ("37° C.") have 44% of CD41+/CD42+ mature megakaryocytes. These results suggest that the pyrimidoindole compound blocks the hyperthermia-induced differentiation of CD34+ cells before the mature CD41+/CD42+ megakaryocyte stage, and/or preferentially expands and maintains CD34+/CD41+ megakaryocytic progenitors. Accordingly, in some embodiments, the pyrimidoindole compound may be removed and the cells may be further propagated under conditions of mild hyperthermia, thereby producing a more synchronized cell population.

Without being bound by theory, the distribution of the cell phenotypes obtained when mild hyperthermia and PIC were combined strongly suggests that both effectors act in synergy to push towards and maintain the CD34+ cell differentiation towards the megakaryocytic lineage up to the progenitor level, so that after 14 days of culture, CD34+/CD41+ MKPs represent the majority of the cells in the entire population.

Example 4

Combination of Culture Under Mild Hyperthermia and Pyrimidoindole Compound Enhances the Number of CFU-MKs Starting with purified CD34+ cells isolated and cultured as described in Example 2, the effect of a 39° C. incubation temperature and of the PIC pyrimidoindole compound, alone or in combination, on the number of CFU-MK obtained, was analyzed by a standard progenitor cell assay as described in Example 1.4.

Figure 2:
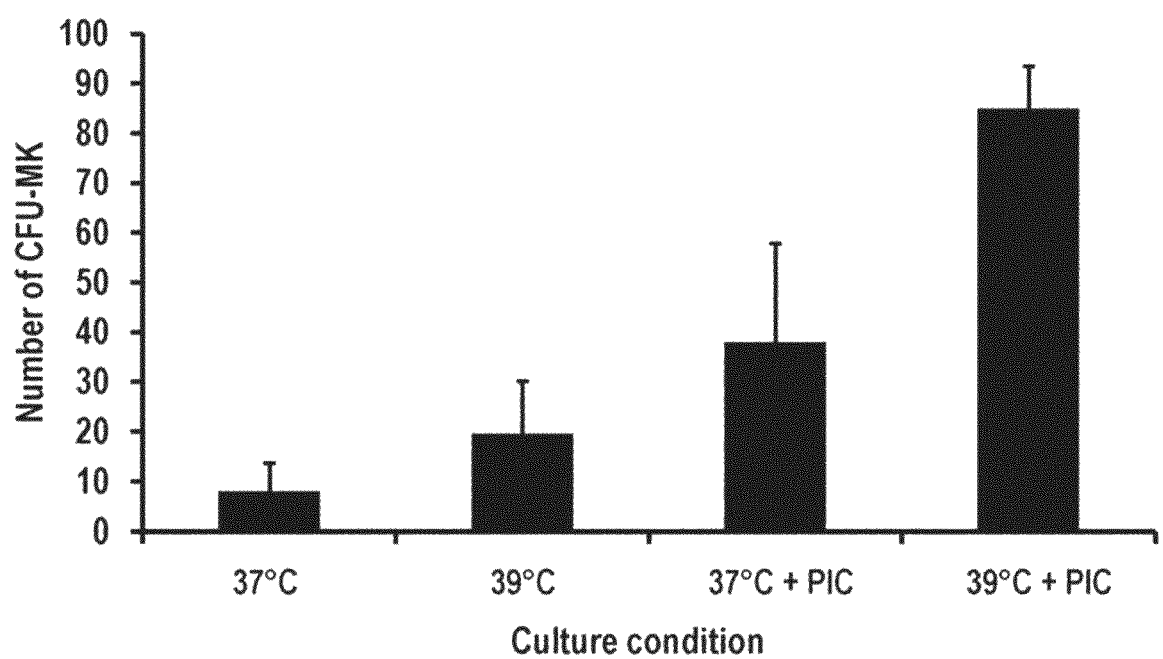
FIG. 2 shows the number of megakaryocytic colony-forming units (CFU-MK) produced under the four culture conditions tested in FIG. 1, as determined by a standard CFU-MK assay.

As shown in FIG. 2, the combined effect of a 39° C. incubation temperature and PIC ("39° C.+PIC") produced a greater number of CFU-MK, as compared to either condition tested individually ("39° C." or "37° C.+PIC"). More particularly, the number of CFU-MK obtained for "39° C.+PIC" was more than twice that obtained when the culture was grown at 37° C. with PIC ("37° C.+PIC"), and more than four times the number of CFU-MK obtained when the culture was grown at 39° C. in the absence of PIC ("39° C."). Furthermore, the number of CFU-MK obtained from cells cultured at 39° C. with PIC ("39° C.+PIC") was greater than that obtainable by adding the number of CFU-MKs of either condition tested individually ("39° C." and "37° C.+PIC"). These results show that the combination of mild hyperthermia and PIC synergized so as to increase the number of CFU-MK obtained. This unforeseen effect is particularly interesting, since current technologies are inefficient at expanding cells with CFU-MK potential in vitro.

Example 5

Combination of Culture Under Mild Hyperthermia and Pyrimidoindole Compound PIC Increases Expansion of CD34+ Cells while Maintaining their Primitive Phenotype CD34+ cells were isolated and cultured in a medium suitable for maintaining their self-renewal while limiting their differentiation into progenitors (StemSpan™ ACF supplemented with StemSpan™ CC110 cytokine cocktail, as described in Example 1.2). The CD34+ cells were cultured at either 37° C. or 39° C., in the presence of a cell culture medium supplemented or not with 35 nM (final concentration) of the pyrimidoindole compound PIC.

Figure 3:
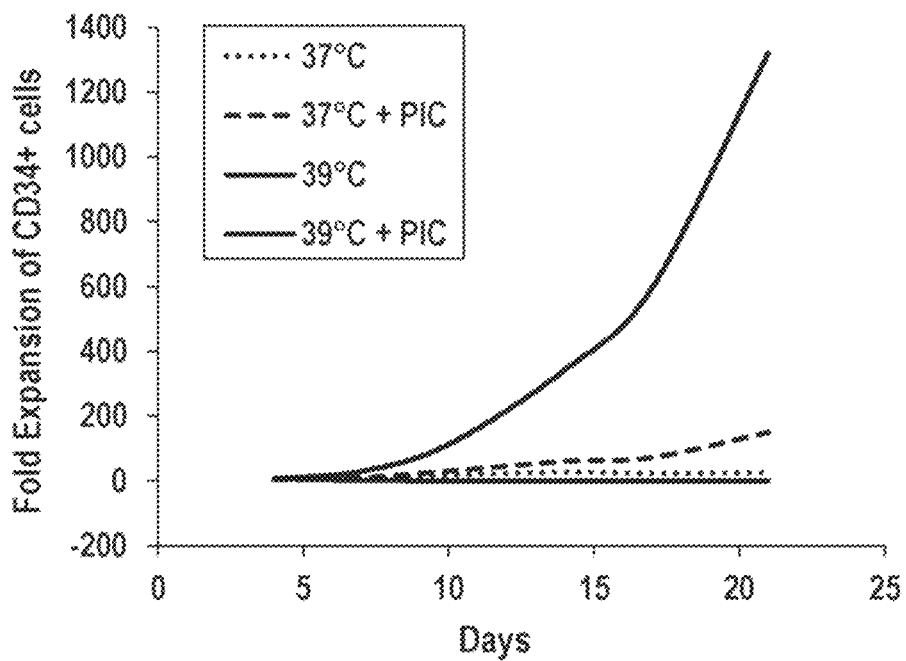
FIG. 3(A) shows fold expansion of CD34+ hematopoietic stem cells as a function of time for CD34+ cells cultured under conditions that promote hematopoietic stem cell expansion while limiting differentiation. Four conditions were tested: (1) "37° C.": at standard temperature in the absence of a pyrimidoindole derivative agonist of hematopoietic stem cell expansion (PIC); (2) "37° C.+PIC": at standard temperature in the presence of 35 nM PIC; (3) "39° C.": under mild hyperthermia in the absence of PIC; or (4) "39° C.+PIC": under mild hyperthermia in the presence of 35 nM PIC.
FIG. 3(B) shows fold expansion of CD34+/CD45RA− long-term hematopoietic stem cells (LT-HSCs) as a function of time starting with an initial population of purified CD34+ cells cultured under conditions that promote hematopoietic stem cell expansion while limiting differentiation. Four conditions were tested: (1) "37° C.": at standard temperature in the absence of a pyrimidoindole derivative agonist of hematopoietic stem cell expansion (PIC); (2) "37° C.+PIC": at standard temperature in the presence of 35 nM PIC; (3) "39° C.": under mild hyperthermia in the absence of PIC; or (4) "39° C.+PIC": under mild hyperthermia in the presence of 35 nM PIC.
Figure 3:
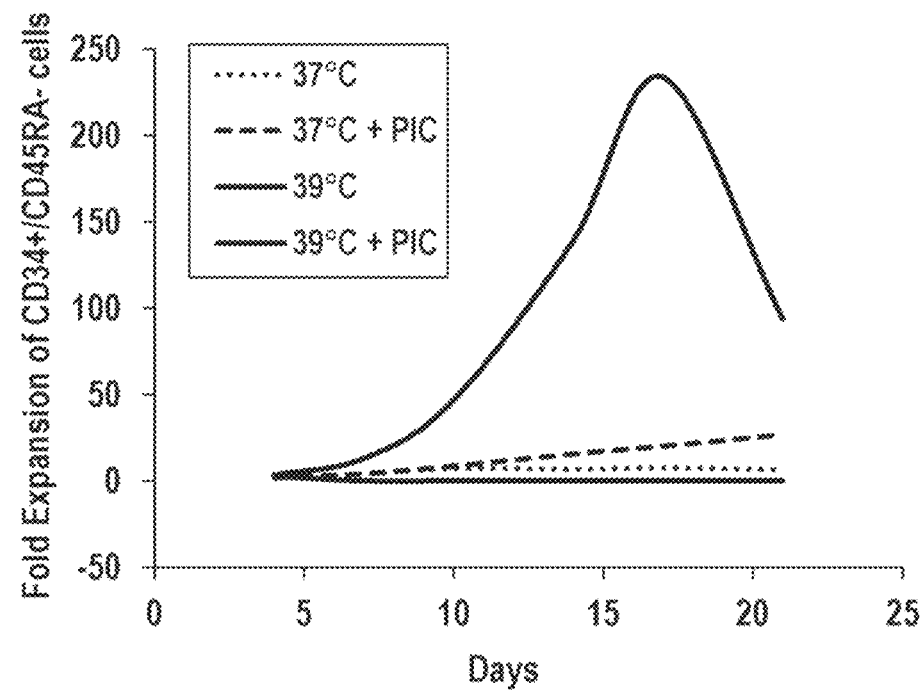

As shown in FIG. 3(A), cells cultured at 37° C. without PIC ("37° C.") yielded modest expansion of CD34+ cells at any time during the culture. Supplementing the cell culture medium with PIC increased the expansion to 100-200—fold on day 21. Strikingly, while cells cultured at 39° C. without PIC ("39° C.") yielded minimal cellular expansion of CD34+ cells, culturing the cells at 39° C. in the presence of PIC ("39° C.+PIC") resulted in a dramatic increase in CD34+ cell expansion, with more than a 1000-fold expansion on day 21. These results show a potent synergistic effect of mild hyperthermia and a pyrimidoindole compound on the expansion of CD34+ cells.

Cell phenotypic profiles of the expanded CD34+ cells were determined on days 4, 7, 10, 14, 17, and 21 by flow cytometry as described in Example 1.3. The results are summarized in Table 2, which shows the percentage of cells bearing the indicated cell surface marker or combination of markers.

sion of CD34+/CD45RA− LT-HSCs. As shown in FIG. 3(B), the expansion of CD34+/CD45RA− LT-HSCs was potently enhanced by culturing cells at 39° C. in the presence of the PIC compound ("39° C.+PIC"). This result demonstrates that the synergistic effect of mild hyperthermia and a pyrimidoindole agonist of hematopoietic stem cell expansion could be exploited for a variety of purposes and for the derivation of several hematopoietic lineages.

Example 6

Materials and Methods for Examples 7-16

6.1 Sources of CD34+ Cells

Human cord blood (CB) was collected after obtaining written informed consent from donors, following our institutional Research Ethics Committee guidelines. Mononuclear cells (MNCs) were first separated over a Ficoll-

TABLE 2

Phenotypic analysis of CD34+ cells cultured in conditions favoring CD34+ cell expansion with limited differentiation

| Day of culture | Conditions | Percentage of cells bearing cell surface marker(s) | | | | | | | |
|---|---|---|---|---|---|---|---|---|---|
| | | CD34+ | CD41+ | CD42+ | CD45RA+ | CD34+/CD45RA− | CD235+ | CD34+/CD41+ | CD34+/CD235+ |
| Day 4 | 37° C. | 94.30 | 8.14 | 2.32 | 68.21 | | 5.44 | 7.67 | 5.10 |
| | 37° C. + PIC | 97.91 | 12.53 | 1.08 | 65.34 | | 4.87 | 12.51 | 4.83 |
| | 39° C. | 85.81 | 7.92 | 4.16 | 62.68 | | 8.62 | 5.03 | 5.94 |
| | 39° C. + PIC | 94.74 | 9.05 | 2.21 | 57.92 | | 4.11 | 8.37 | 3.65 |
| Day 7 | 37° C. | 80.38 | 13.62 | 5.13 | 68.46 | | 9.42 | 12.10 | 8.18 |
| | 37° C. + PIC | 94.61 | 15.93 | 1.30 | 80.07 | | 5.42 | 15.74 | 5.28 |
| | 39° C. | 85.29 | 10.83 | 13.94 | 95.42 | | 13.94 | 9.44 | 13.00 |
| | 39° C. + PIC | 88.27 | 18.12 | 2.92 | 74.14 | | 10.89 | 16.17 | 9.68 |
| Day 10 | 37° C. | 34.46 | 12.95 | 8.58 | 79.08 | | 5.41 | 8.80 | 2.82 |
| | 37° C. + PIC | 84.26 | 14.19 | 0.48 | 88.37 | | 2.33 | 12.94 | 2.16 |
| | 39° C. | —* | —* | —* | —* | —* | —* | —* | —* |
| | 39° C. + PIC | 71.28 | 27.40 | 1.35 | 82.34 | | 9.36 | 20.80 | 7.94 |
| Day 14 | 37° C. | 20.49 | 8.14 | 3.61 | 71.95 | 5.26 | 4.09 | 4.37 | 1.90 |
| | 37° C. + PIC | 58.28 | 15.16 | 0.19 | 84.63 | 15.22 | 2.10 | 9.55 | 1.39 |
| | 39° C. | —* | —* | —* | —* | —* | —* | —* | —* |
| | 39° C. + PIC | 48.58 | 32.04 | 1.16 | 81.97 | 19.74 | 5.13 | 13.88 | 3.72 |
| Day 17 | 37° C. | 13.03 | 9.43 | 1.84 | 76.57 | 4.38 | 5.24 | 2.30 | 2.04 |
| | 37° C. + PIC | 48.29 | 24.70 | 0.63 | 87.89 | 13.58 | 3.94 | 9.75 | 0.52 |
| | 39° C. | —* | —* | —* | —* | —* | —* | —* | —* |
| | 39° C. + PIC | | | | | | | | |
| Day 21 | 37° C. | | | | | | | | |
| | 37° C. + PIC | | | | | | | | |
| | 39° C. | —* | —* | —* | —* | —* | —* | —* | —* |
| | 39° C. + PIC | | | | | | | | |

*N/D: Not determined.

The results of the phenotypic analysis presented in Table 2 indicate that the combined treatment of mild hyperthermia and PIC did not lead to an enhanced differentiation of the cells towards the megakaryocytic and erythroid (CD235+) lineages, which suggests that "stemness" was maintained to some extent. Without being bound by theory, these results collectively suggest that mild hyperthermia combined with the use of a pyrimidoindole compound preserves the anti-differentiation effects of the pyrimidoindole compound, while simultaneously potentiating the stimulatory effects of the 39° C. incubation temperature on the in vitro expansion of the cells.

The results presented in FIG. 3(A) are derived from the entire population of CD34+ cells. A minor population of CD34+/CD45RA− cells are thought to represent genuine long-term hematopoietic stem cells (LT-HSCs). Combining the results of total cell expansion and those of Table 2 allowed to determine the absolute numbers and fold expan- Hypaque™ density gradient (GE Healthcare), then cryopreserved at −180° C. in Cryostor CS10™ medium (STEMCELL Technologies). Thawed MNCs from six to eight CB were pooled before CD34 isolation. CB CD34+ cells were enriched by positive selection using the EasySep™ CD34 enrichment kit, according to the manufacturer's instructions (STEMCELL Technologies).

Human bone marrow and G-CSF-mobilized peripheral blood CD34+ cells were purchased from AllCells.

6.2 Culture and Differentiation of CD34+-Enriched Cells Towards the Megakaryocytic Lineage Human CD34+-enriched cells (purity ≥90%) were seeded in 24-well plates at 100 000 cells/mL in expansion medium consisting of either (1) StemSpan™ ACF (ACF; STEMCELL Technologies) supplemented with the OMPC cytokine cocktail (Robert et al., 2011), or (2) StemSpan™ SFEM (STEMCELL Technologies) supplemented with the BS1 megakaryocyte expansion and differentiation cocktail (Cortin et al., 2005). OMPC consists of 35 ng/mL thrombopoietin (TPO; Feldan Therapeutics), 10 ng/mL stem cell factor (SCF; Peprotech), and 11 ng/mL human FMS-like tyrosine kinase 3 ligand (FLT3, Peprotech). BS1 consists of 1 ng/mL SCF, 30 ng/mL TPO, 7.5 ng/mL IL-6 and 13.5 ng/mL IL-9 (Feldan Therapeutics).

Cultures were maintained in a humidified atmosphere with 5% $CO_2$ at 37° C. or 39° C., as indicated in the Examples. Cells were diluted at 300 000 cells/mL with fresh medium every 3 to 4 days. Stock solutions of PIC and PIC2 were prepared by dissolving in DMSO, then added directly to cultured cells at the following final effective concentrations: PIC: 35 nM (see Example 2); PIC2: 500 nM (see Example 7.4).

6.3 Culture and Differentiation of CD34+-Enriched Cells Towards the Erythroid Lineage Human CB CD34+-enriched cells (purity ≥90%) were seeded in 24-well plates at 100 000 cells/mL in expansion medium consisting of Eave's basal medium (Iscove's modified Dulbecco's medium (IMDM), 20% BIT (10 ng/mL bovine serum albumin, 10 µg/mL bovine pancreatic insulin, 200 µg/mL human transferrin; STEMCELL Technologies), 0.1 mg/mL low-density lipoprotein (STEMCELL Technologies), 50 µM 2-mercaptoethanol) supplemented with 20 ng/mL SCF (Peprotech) and 2 U/mL erythropoietin (EPO; Feldan Therapeutics). Cultures were maintained in a humidified atmosphere with 5% $CO_2$ at 37° C. or 39° C., as indicated in the Examples. Cells were diluted at 300 000 cells/mL with fresh medium every 3 to 4 days. A stock solution of PIC was prepared by dissolving in DMSO, then added directly to cultured cells at a final effective concentration of 35 nM.

6.4 Culture of CD34+-Enriched Hematopoietic Stem Cells in Conditions Favoring Self-Renewal Human CD34+-enriched cells (purity ≥90%) were seeded in 24- or 96-well plates at 500 000 cells/mL in one of three expansion media consisting of StemSpan™ ACF (ACF), SFEM, or SFEM II (STEMCELL Technologies), supplemented with either CC110 (STEMCELL Technologies) or a home-made (HM) cytokine cocktail consisting of 100 ng/mL human FLT3 (Peprotech), 100 ng/mL SCF (Peprotech), 50 ng/mL TPO (Feldan Therapeutics) and 10 µg/mL low-density lipoprotein (LDL, STEMCELL Technologies). Cultures were maintained in a humidified atmosphere with 5% $CO_2$ at 37° C. or 39° C., as indicated in the Examples. Cells were diluted at 500 000 cells/mL with fresh medium every 3 to 4 days. Stock solutions of PIC and PIC2 were prepared by dissolving in DMSO, then added directly to cultured cells at the following final effective concentrations: PIC: 35 nM; PIC2: 500 nM.

6.5 Analysis of Cultured Cells

Cellular counts and viability were determined by adding Solution 18 (Acridine Orange and DAPI solution, ChemomMetec) and using NucleoCounter™ NC-250 for detection (ChemomMetec).

For cells expanded in conditions favoring differentiation towards the MK lineage, surface markers were detected using the following antibodies: CD34-FITC, CD41a-APC and CD42b-PE. All antibodies were purchased from BD Biosciences, except for CD34-FITC which was purchased from Immunotech. 7AAD was used as a viability dye. All samples were analyzed on an Accuri™ C6 flow cytometer (BD Biosciences), and raw data were analyzed with FCS Express 5 Flow Research Edition software from at least 15 000 viable cell events acquired for each sample. Colony-forming-unit megakaryocytes (CFU-MK) were assayed using MegaCult-C™, according to the manufacturer's instructions (STEMCELL Technologies).

For cells expanded in conditions favoring differentiation towards the erythroid lineage, surface markers were detected using the following antibodies: CD34-FITC, CD71-APC and CD235-PE. All antibodies were purchased from BD Biosciences, except for CD34-FITC which was purchased from Immunotech. 7AAD was used as a viability dye. All samples were analyzed on an Accuri™ C6 flow cytometer (BD Biosciences), and raw data were analyzed with FCS Express 5 Flow Research Edition software from at least 15 000 viable cell events acquired for each sample.

For cells expanded in conditions favoring self-renewal, surface markers were detected using the following antibodies: CD34-PE, CD45RA-FITC, and CD38-BV421. All antibodies were purchased from BD Biosciences, except for CD34-PE which was purchased from Immunotech. Labeling of aldehyde dehydrogenase (ALDH)-positive cells was performed using the ALDEFLUOR™ Kit (STEMCELL Technologies), according to the manufacturer's instructions. 7AAD was used as a viability dye. All samples were analyzed on a FACS-Cy Flow ML system (Sysmex), and raw data were analyzed with FCS Express 5 Flow Research Edition software from at least 15 000 viable cell events acquired for each sample.

6.6 Transplantation of CD41+ Cells into Mice, and Evaluation of Bone Marrow Engraftment Seven to nine weeks old female NOD.Cg-Prkdc$^{scid}$ Il2rg$^{tm1Wjl}$/SzJ (NSG) mice were purchased from The Jackson Laboratory (Bar Harbor, Me.). Sublethally irradiated mice (250 cGy, $^{137}$Cs) were transplanted intravenously by tail vein injection with CB CD34+-enriched cells expanded in StemSpan™ SFEM medium supplemented with the BS1 cocktail for 10 days. Each experiment included mice injected with PBS as negative control for bone marrow engraftment. Experimental and control groups for evaluation of bone marrow (BM) engraftment and human platelet production consisted of at least 6 mice. Engraftment of human cells in the bone marrow of mice was evaluated between 12 to 16 weeks post-transplantation by flushing femurs and tibias and analyzing freshly isolated BM cells by flow cytometry using the following antibodies: human CD45-PE-Cy7, mouse CD45-PE, human CD41-APC, human CD33-APC, human CD34-PE, human CD235-PE, human CD3-FITC. 7AAD was used as a viability dye. Red cells were lysed using BD Lysing solution following the manufacturer's instructions.

6.7 Analysis of Human Platelet Production in Transplanted Mice

Retro-orbital venous plexus blood was collected from anesthetized mice using EDTA-coated capillaries (Drummond). The evaluation of human platelet production in transplanted mice consisted of two distinct steps. First, murine platelet counts were determined by staining murine platelets with a rat anti-mouse CD41-FITC antibody in whole blood. Samples were then brought to a final dilution of 1/18 000 in PBS/1% BSA, and the concentration of murine platelets was assayed by flow cytometry using the BD Accuri™ C6 instrument. Second, the proportion of human platelets was measured in platelet-rich plasma (PRP). PRP was prepared by diluting whole blood in PBS (½) and centrifuging for 30 seconds at 800 RPM. Ten microliters of PRP was stained with mouse anti-human CD41-APC and rat anti-mouse CD41-FITC antibodies. Samples were then analyzed on the BD Accuri™ C6 instrument; at least 400 000 events were acquired in the platelet region of the dot-plot.

6.8 Transplantation into Mice of Fresh CB CD34+ Cells, or Progenies Thereof Obtained by In Vitro Culture of CB CD34+ Cells in Conditions Favoring Self-Renewal, and Evaluation of Bone Marrow Engraftment Seven to nine weeks old female NOD.Cg-Prkdc$^{scid}$ Il2rgm$^{tm1Wjl}$/SzJ (NSG) mice were purchased from The Jackson Laboratory (Bar Harbor, Me.). Sublethally irradiated mice (250 cGy, $^{137}$Cs) were transplanted intravenously by tail vein injection with either fresh CD34+-enriched CB cells, or their total cell progeny that had been in vitro-expanded for 12 days. Each experiment included mice injected with PBS as negative control for bone marrow engraftment. Experimental and control groups consisted of at least 5 mice. Engraftment of human cells in the bone marrow of mice was evaluated at 27 weeks post-transplantation by flushing femurs and tibias and analyzing freshly isolated BM cells by flow cytometry using the following antibodies: human CD45-PE-Cy7, mouse CD45-PE, human CD33-BV421, human CD19-FITC, human CD34-PE, and human CD3-FITC. 7AAD was used as a viability dye.

Example 7

Effect of Different Sources of CD34+ Cells on Expansion of CD34+/CD41+ Megakaryocytic Progenitors Under Mild Hyperthermia and Pyrimidoindole Compounds 7.1 Combined Use of Mild Hyperthermia and PIC Results in Synergistic Expansion of Megakaryocytic Progenitors from Cord Blood CD34+ Cells Human CD34+-enriched cells were obtained from human cord blood (CB) as described in Example 6.1, and were cultured in StemSpan™ ACF medium supplemented with the OMPC cytokine cocktail as described in Example 6.2 in the presence or absence of mild hyperthermia (39° C.) and/or the presence or absence of the pyrimidoindole compound PIC (see Example 2). Cellular counts and viability were determined as described in Example 6.5.

Figure 4:
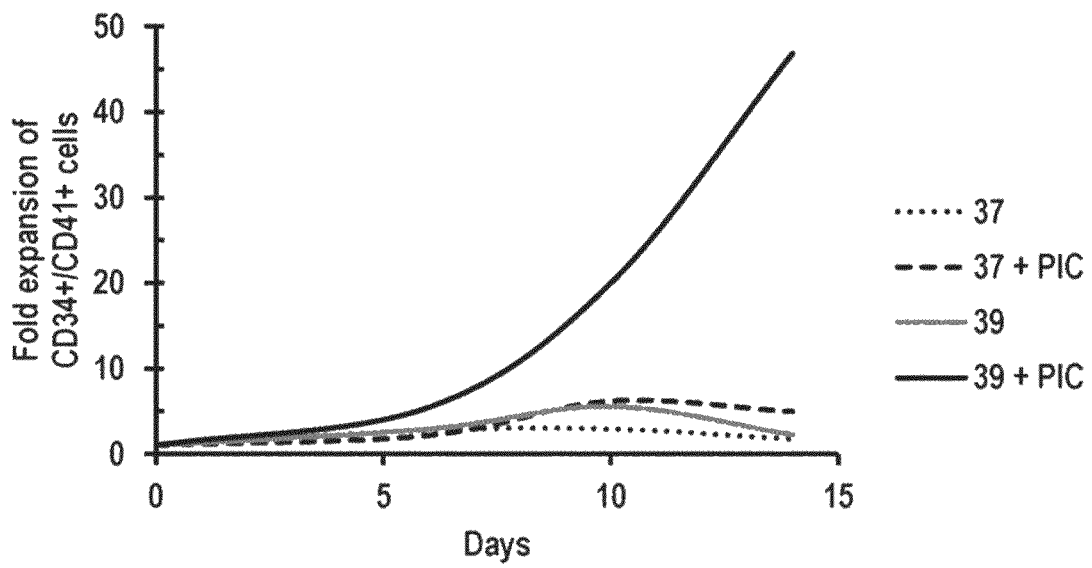
FIGS. 4-6 show the fold expansion of CD34+/CD41+ cells (megakaryocytic progenitors) over 14 days in the presence ("39") or absence ("37") of mild hyperthermia and/or the presence or absence of PIC. Expansions were performed from cord blood CD34+ cells (FIG. 4), mobilized peripheral blood CD34+ cells (FIG. 5), or bone marrow CD34+ cells (FIG. 6).

FIG. 4 shows the fold expansion of CD34+/CD41+ cells (megakaryocytic progenitors) under the different culture conditions tested over 14 days. These results show a synergistic effect of the combined use of mild hyperthermia (39° C.) and PIC on the expansion of CD34+/CD41+ cells from cord blood CD34+ cells.

7.2 Combined Use of Mild Hyperthermia and PIC Results in Synergistic Expansion of Megakaryocytic Progenitors from Mobilized Peripheral Blood CD34+ Cells Human G-CSF-mobilized peripheral blood CD34+ cells were obtained as described in Example 6.1, and were cultured in StemSpan™ SFEM medium supplemented with the BS1 megakaryocyte expansion and differentiation cocktail as described in Example 6.2 in the presence or absence of mild hyperthermia (39° C.) and/or the presence or absence of the pyrimidoindole compound PIC (see Example 2). Cellular counts and viability were determined as described in Example 6.5.

Figure 5:
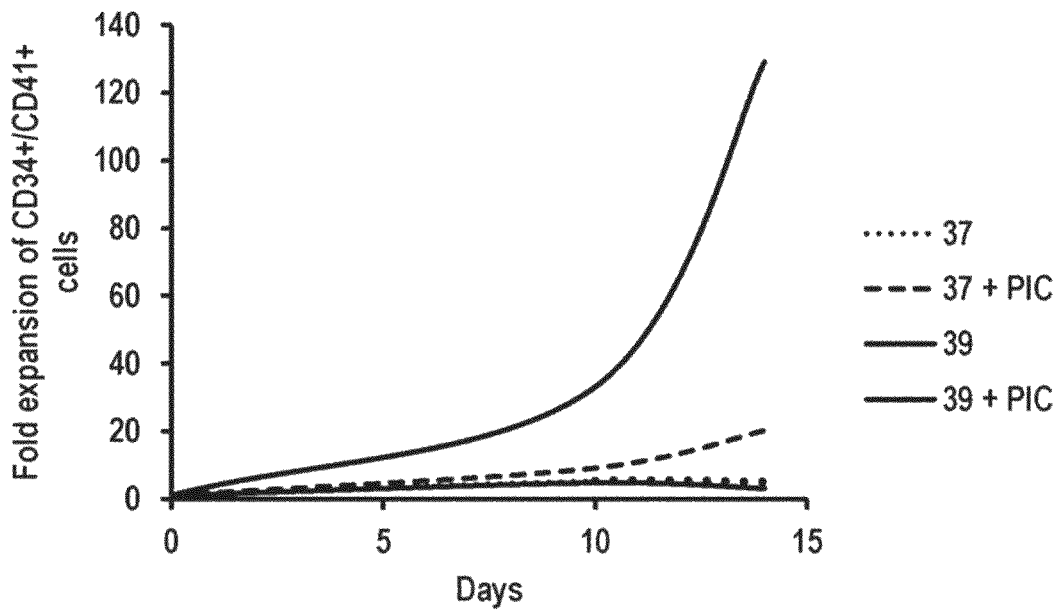

FIG. 5 shows the fold expansion of CD34+/CD41+ cells (megakaryocytic progenitors) under the different culture conditions tested over 14 days. These results show a synergistic effect of the combined use of mild hyperthermia (39° C.) and PIC on the expansion of CD34+/CD41+ cells from mobilized peripheral blood CD34+ cells.

7.3 Combined Use of Mild Hyperthermia and PIC Results in Synergistic Expansion of Megakaryocytic Progenitors from Bone Marrow CD34+ Cells Human bone marrow CD34+ cells were obtained as described in Example 6.1, and were cultured in StemSpan™ SFEM medium supplemented with the BS1 megakaryocyte expansion and differentiation cocktail as described in Example 6.2 in the presence or absence of mild hyperthermia (39° C.) and/or the presence or absence of the pyrimidoindole compound PIC (see Example 2). Cellular counts and viability were determined as described in Example 6.5.

Figure 6:
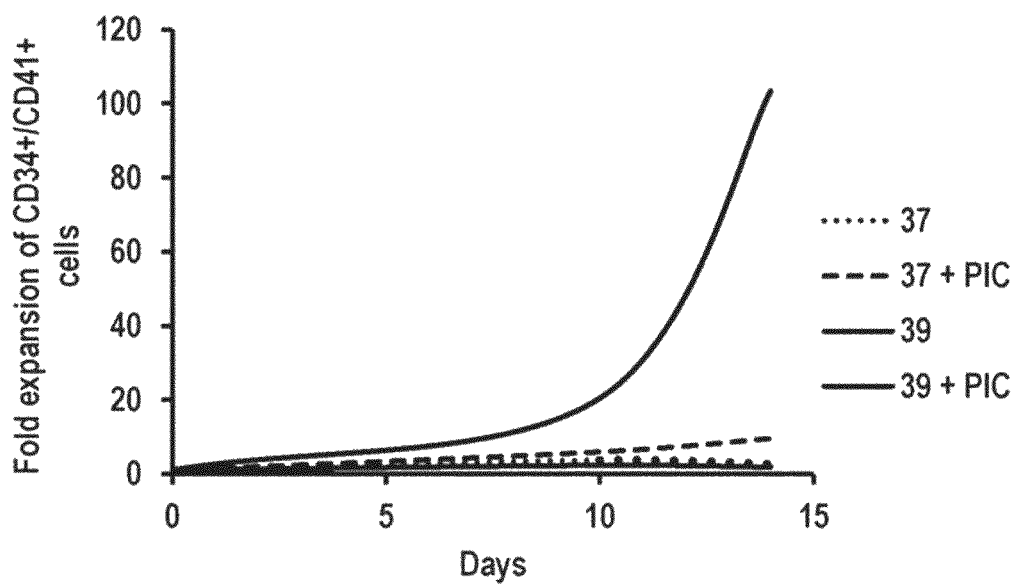

FIG. 6 shows the fold expansion of CD34+/CD41+ cells (megakaryocytic progenitors) under the different culture conditions tested over 14 days. These results show a synergistic effect of the combined use of mild hyperthermia (39° C.) and PIC on the expansion of CD34+/CD41+ cells from bone marrow CD34+ cells.

7.4 Combined Use of Mild Hyperthermia and PIC2 Results in Synergistic Expansion of Megakaryocytic Progenitors from Cord Blood CD34+ Cells Human CD34+-enriched cells were obtained from human cord blood (CB) as described in Example 6.1, and were cultured in StemSpan™ SFEM medium supplemented with the BS1 cytokine cocktail as described in Example 6.2 in the presence or absence of mild hyperthermia (39° C.) and/or the presence or absence of the pyrimidoindole compound "PIC2":

Methyl 4-((3-(piperidin-1-yl)propyl)amino)-9H-pyrimido [4,5-b] indole-7-carboxylate ("UM729").

Cellular counts and viability were determined as described in Example 6.5.

Figure 7:
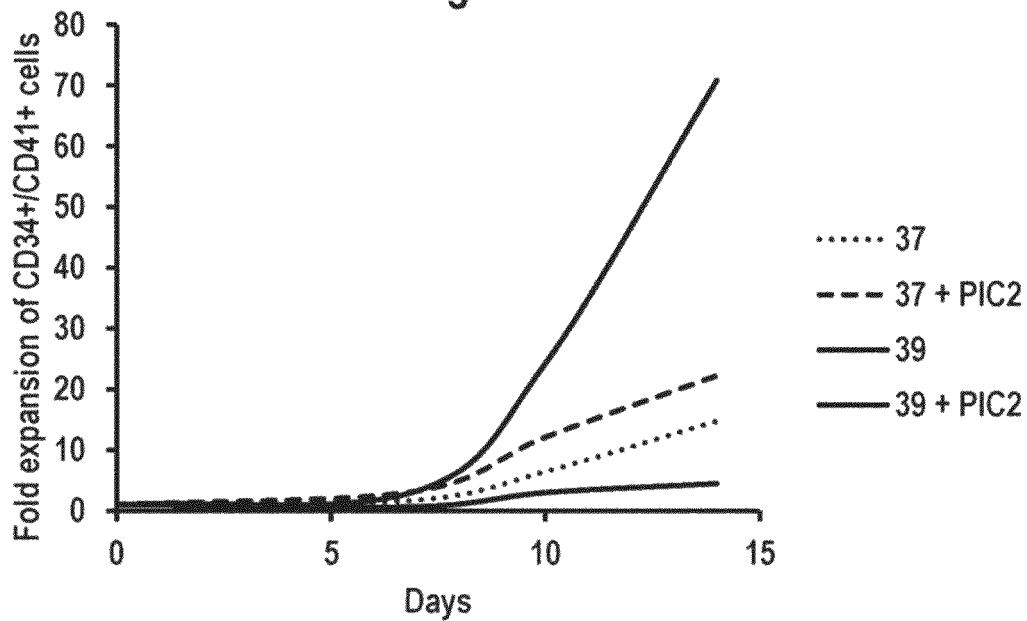
FIG. 7 shows the fold expansion of CD34+/CD41+ cells (megakaryocytic progenitors) over 14 days in the presence ("39") or absence ("37") of mild hyperthermia and/or the presence or absence of another pyrimidoindole derivative agonist of hematopoietic stem cell expansion (PIC2).

FIG. 7 shows the fold expansion of CD34+/CD41+ cells (megakaryocytic progenitors) under the different culture conditions tested over 14 days. These results show a synergistic effect of the combined use of mild hyperthermia (39° C.) and PIC2 on the expansion of CB CD34+/CD41+ cells.

Example 8

Production of Human Platelets in Mice Following Infusion of In Vitro-Expanded MK Progenitors Human CD41+ cells were prepared by expanding CB CD34+ cells in vitro under mild hyperthermia and in conditions favoring the preferential expansion of MK progenitors, as described in Example 6.2; StemSpan™ SFEM medium was supplemented with the BS1 cytokine cocktail for the in vitro expansion. Measured doses of CD41+ cells obtained after 10 days of culture were transplanted into NSG mice as described in Example 6.6.

Figure 8:
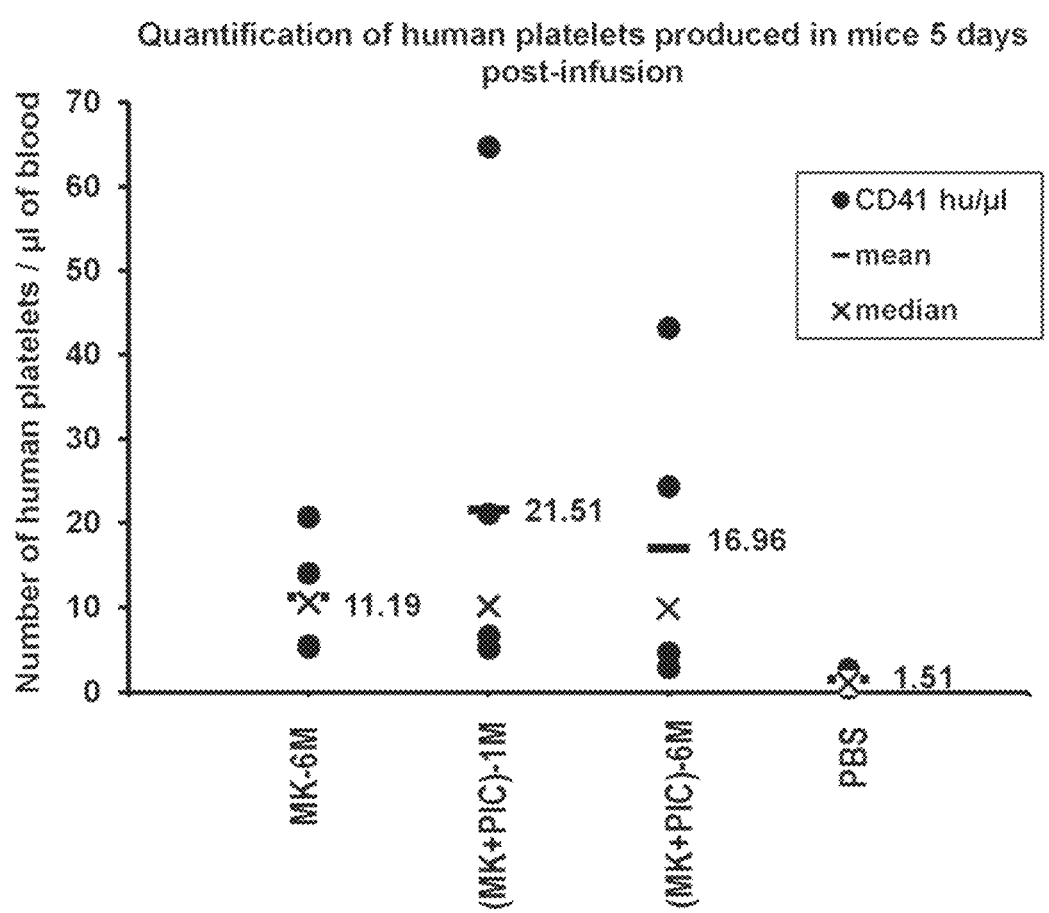
FIGS. 8 and 9 show the results of human platelet production at 5 days and 2.5 weeks, respectively, in immunodeficient mice transplanted with human cord blood CD34+ cells expanded in vitro under conditions of mild hyperthermia and in a culture medium favoring the preferential expansion of megakaryocyte (MK) progenitors (CD41+ cells). "MK-6M": infusion of six million CD41+ cells produced in the absence of PIC; "(MK+PIC)-1M": infusion of one million CD41+ cells produced in the presence of PIC; "(MK+PIC)-6M": infusion of six million CD41+ cells produced in the presence of PIC; and "PBS": infusion of phosphate-buffered saline as a control. The numbers to the right of the dash symbols represent mean numbers of human platelets/µL of blood for each condition.
Figure 9:
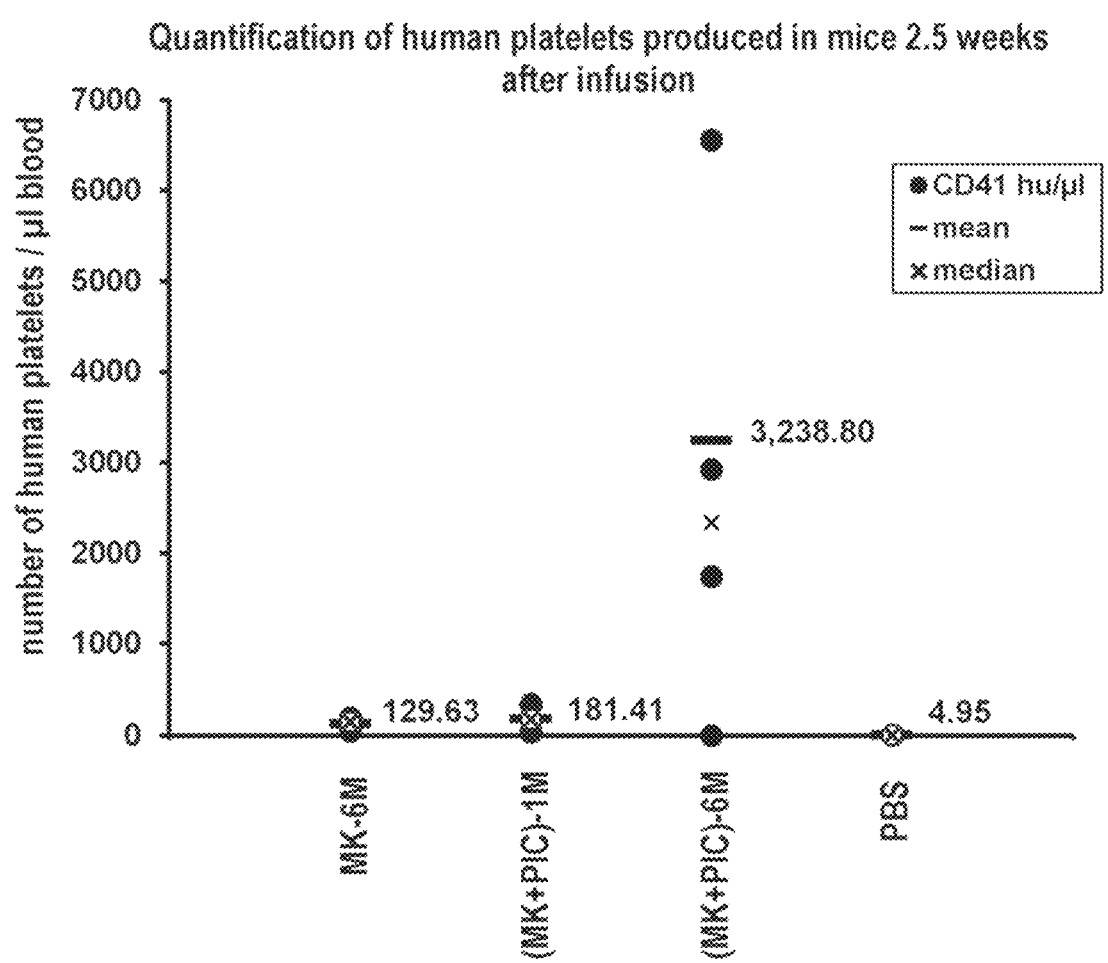

Human platelet production in mice was determined by counting human platelets in murine blood either five days or 2.5 weeks post-infusion of CB CD34+ cells expanded in vitro in conditions favoring the preferential expansion of MK progenitors, as described in Example 6.2. FIGS. 8 and 9 show the results of short-term human platelet production in mice at 5 days and 2.5 weeks, respectively, wherein "MK-6M": infusion of six million CD41+ cells produced using StemSpan™ SFEM+BS1 cocktail; "(MK+PIC)-1M": infusion of one million CD41+ cells produced using StemSpan™ SFEM+BS1 cocktail supplemented with PIC; "(MK+PIC)-6M": infusion of six million CD41+ cells produced using StemSpan™ SFEM+BS1 cocktail supplemented with PIC; and "PBS": infusion of phosphate-buffered saline as a control. The numbers to the right of the dash symbols represent mean numbers of human platelets/µL of blood for each condition.

Example 9

Effect of Erythroid Differentiation Medium on Expansion of CD34+ Cells Under Mild Hyperthermia and PIC Human CD34+-enriched cells were obtained from human cord blood (CB) as described in Example 6.1, and were cultured in an erythroid differentiation medium as described in Example 6.3 in the presence or absence of mild hyperthermia (39° C.) and/or the presence or absence of the pyrimidoindole compound PIC (see Example 2). Cellular counts and viability were determined as described in Example 6.5.

Figure 10:
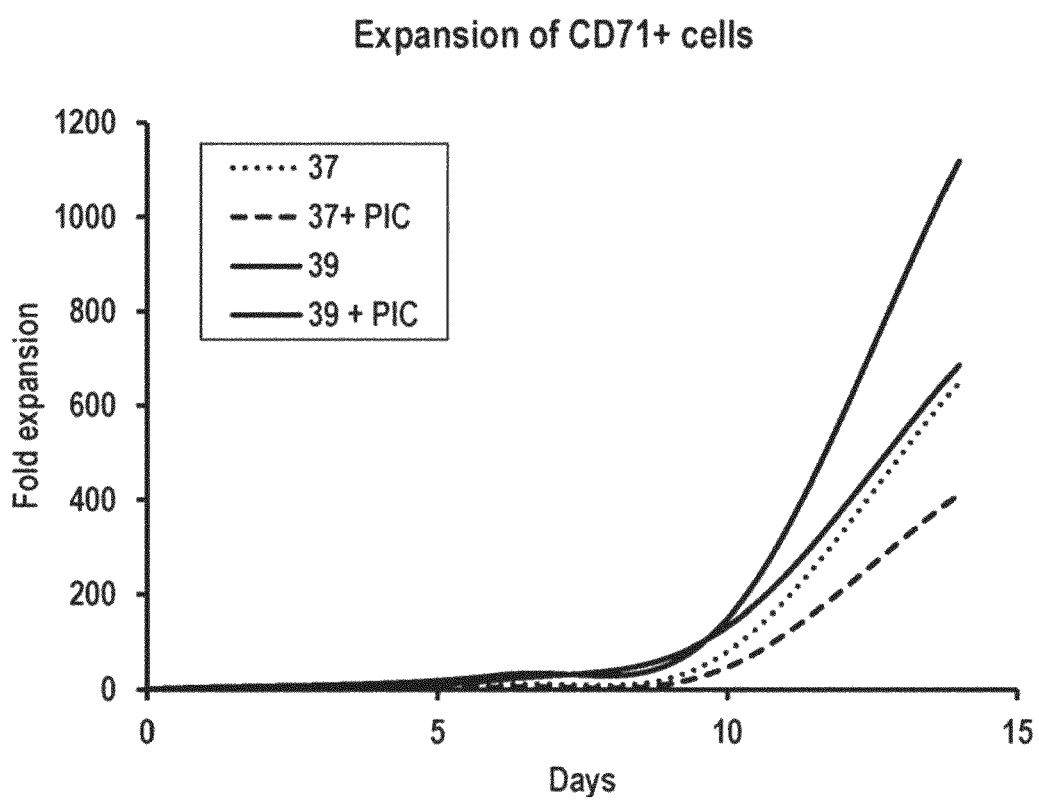
FIG. 10 shows the fold expansion of cord blood-derived CD71+ cells (erythroid precursors) over 14 days in the presence ("39") or absence ("37") of mild hyperthermia and/or the presence or absence of PIC.

9.1 Effect of PIC on Expansion of CD71+ Cells (Erythroid Precursors) in Erythroid Differentiation Medium FIG. 10 shows the fold expansion of CB CD71+ cells (erythroid precursors) under the different culture conditions tested over 14 days. The use of mild hyperthermia (39° C.) resulted in an increase in the expansion of CD71+ erythroid precursors (see FIG. 10, "37" vs. "39", and "37+"PIC" vs. "39+PIC"). However, the addition of PIC resulted in a decrease in the expansion of CD71+ erythroid precursors (see FIG. 10, "37" vs. "37+PIC", and "39" vs. "39+PIC").

Figure 11:
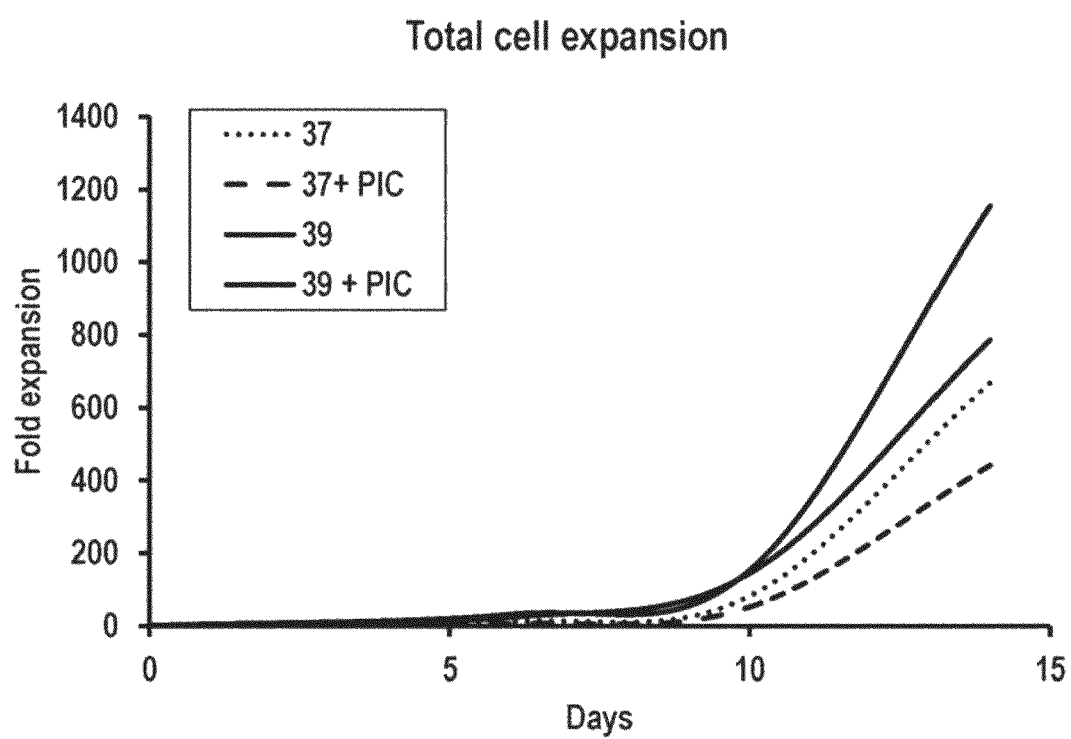
FIG. 11 shows the fold expansion of total cells (total cell expansion) over 14 days in the presence ("39") or absence ("37") of mild hyperthermia and/or the presence or absence of PIC.

FIG. 11 shows the fold expansion of total cells (total cell expansion) under the different culture conditions tested over 14 days. The use of mild hyperthermia (39° C.) resulted in an increase in total cell expansion (see FIG. 11, "37" vs. "39", and "37+PIC" vs. "39+PIC"). However, the addition of PIC resulted in a decrease in total cell expansion (see FIG. 11, "37" vs. "37+PIC", and "39" vs. "39+PIC").

Figure 12:
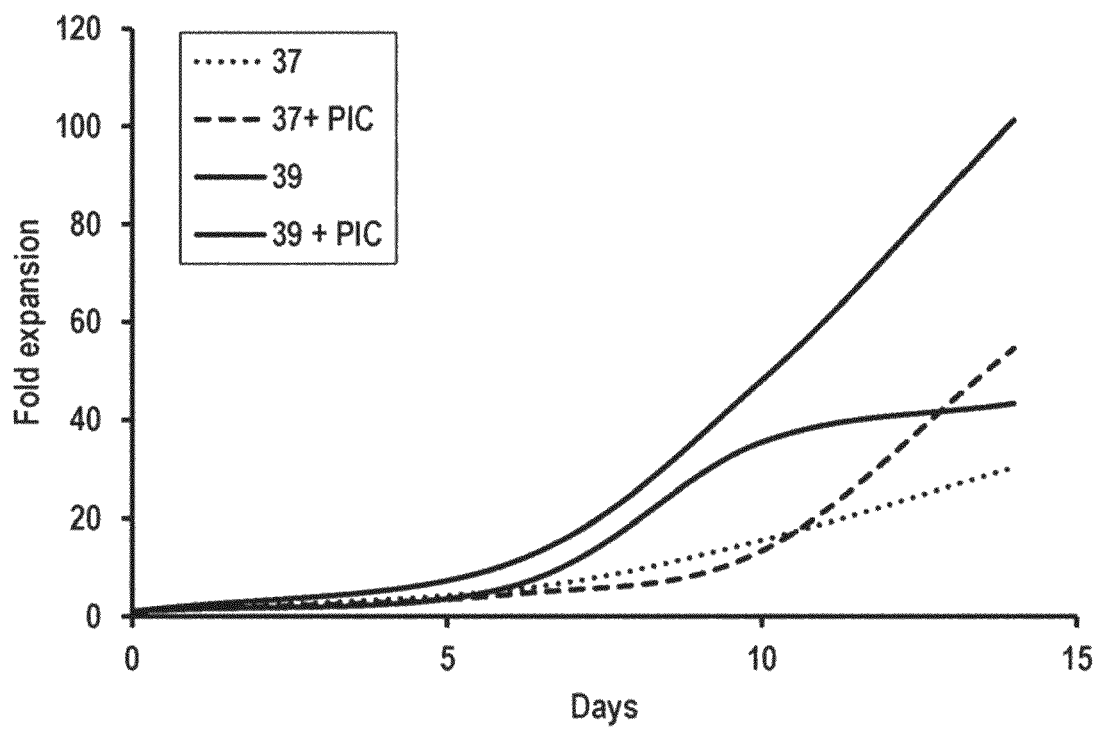
FIGS. 12 and 13 show the fold expansion of CD34+ cells (HSGs) and CD34+/CD71+ cells (erythroid progenitors), respectively, over 14 days in the presence ("39") or absence ("37") of mild hyperthermia and/or the presence or absence of PIC.
Figure 13:
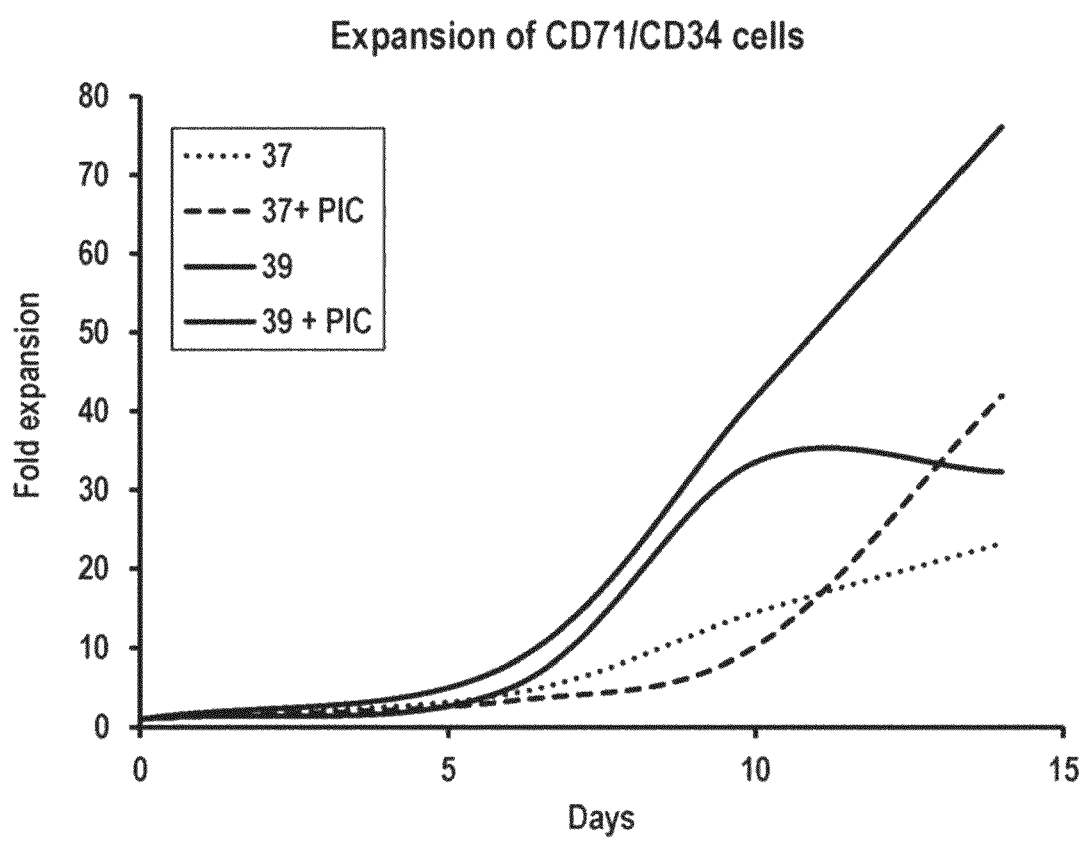

9.2 Additive Effect of Mild Hyperthermia and PIC on Expansion of CD34+ Cells (HSCs) and CD34+/CD71+ Cells (Erythroid Progenitors) in Erythroid Differentiation Medium FIGS. 12 and 13 show the fold expansion of CD34+ cells and CD34+/CD71+ cells (erythroid progenitors), respectively, under the different culture conditions tested over 14 days. Interestingly, these results show that the use of mild hyperthermia (39° C.) and PIC have an additive effect on the expansion of both CB CD34+ cells (FIG. 12) and CB CD34+/CD71+ cells (erythroid progenitors) (FIG. 13) in an erythroid differentiation medium.

Example 10

Effect of Different Cytokine Cocktails on Expansion of CD34+ Cells (HSCs) and CD34+/CD45RA− Cells (LT-HSCs) Under Mild Hyperthermia and PIC The results presented in Example 5 showed that the combined use of mild hyperthermia (39° C.) and PIC resulted in an increase in expansion of CD34+ cells while limiting their differentiation when using StemSpan™ ACF medium supplemented with the commercially available CC110 cytokine cocktail. The results presented in this example show that synergistic expansion of CB CD34+ HSCs under mild hyperthermia (39° C.) and PIC can be obtained using a home-made (HM) cytokine cocktail.

Human CB CD34+-enriched cells were obtained from human cord blood (CB) as described in Example 6.1, and were cultured in conditions favoring their self-renewal as generally described in Example 6.4, in the presence or absence of mild hyperthermia (39° C.) and/or the presence or absence of the pyrimidoindole compound PIC (see Example 2). Cellular counts and viability were determined as described in Example 6.5.

Figure 14:
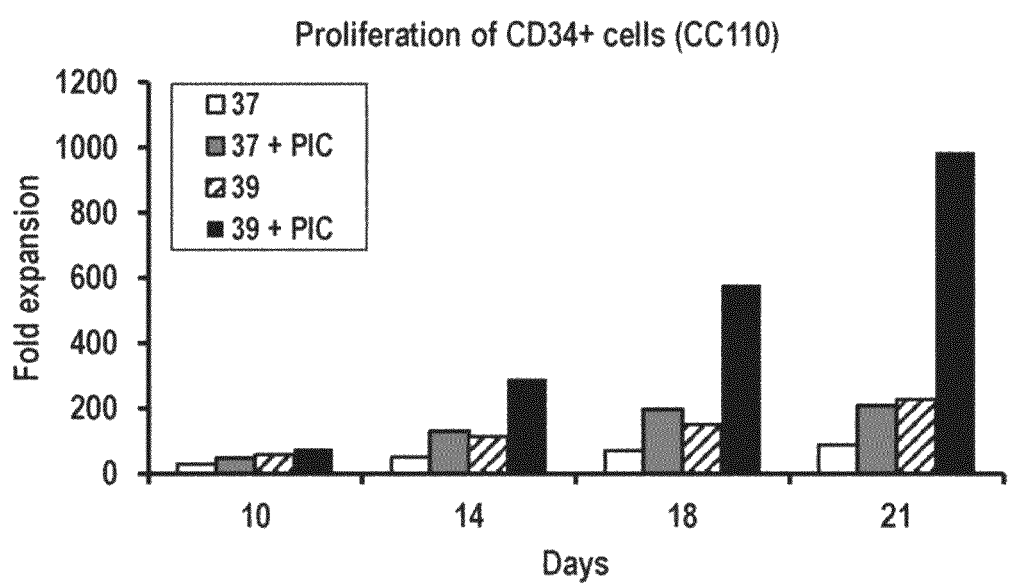
FIG. 14 shows the fold-expansion of cord blood-derived CD34+ cells (hematopoietic stem cells) cultured in medium supplemented with either the commercially available CC110 cytokine cocktail (FIG. 14A) or a home-made (HM) cytokine cocktail (FIG. 14B). The cells were cultured in the presence ("39") or absence ("37") of mild hyperthermia and/or the presence or absence of PIC.
Figure 14:
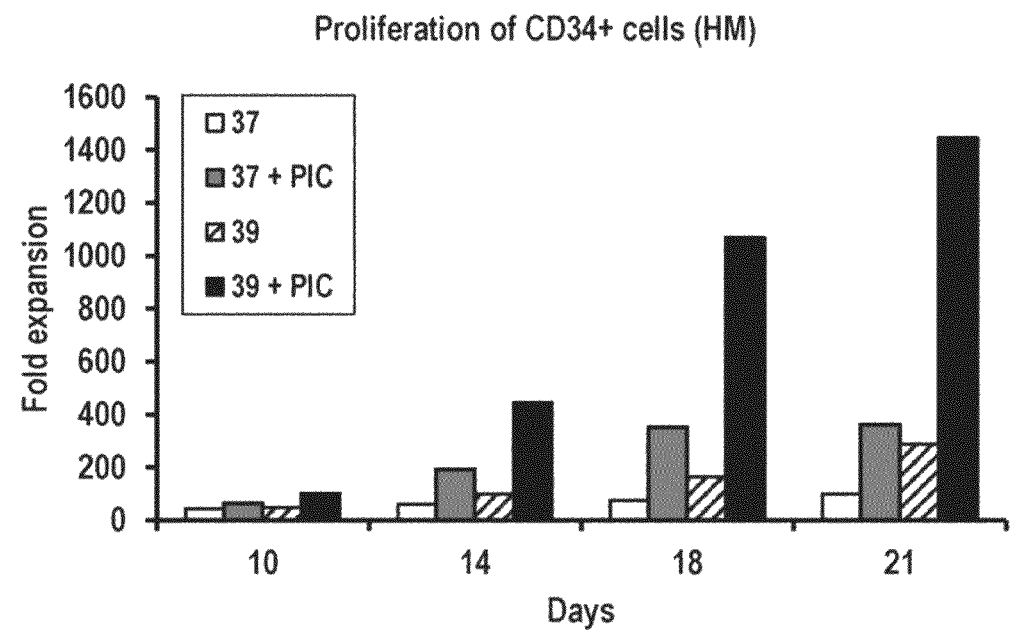

FIG. 14 shows the fold-expansion of CB CD34+ cells (hematopoietic stem cells) cultured in StemSpan™ ACF medium supplemented with either the CC110 cytokine cocktail (FIG. 14A) or the home-made (HM) cytokine cocktail (FIG. 14B).

Figure 15:
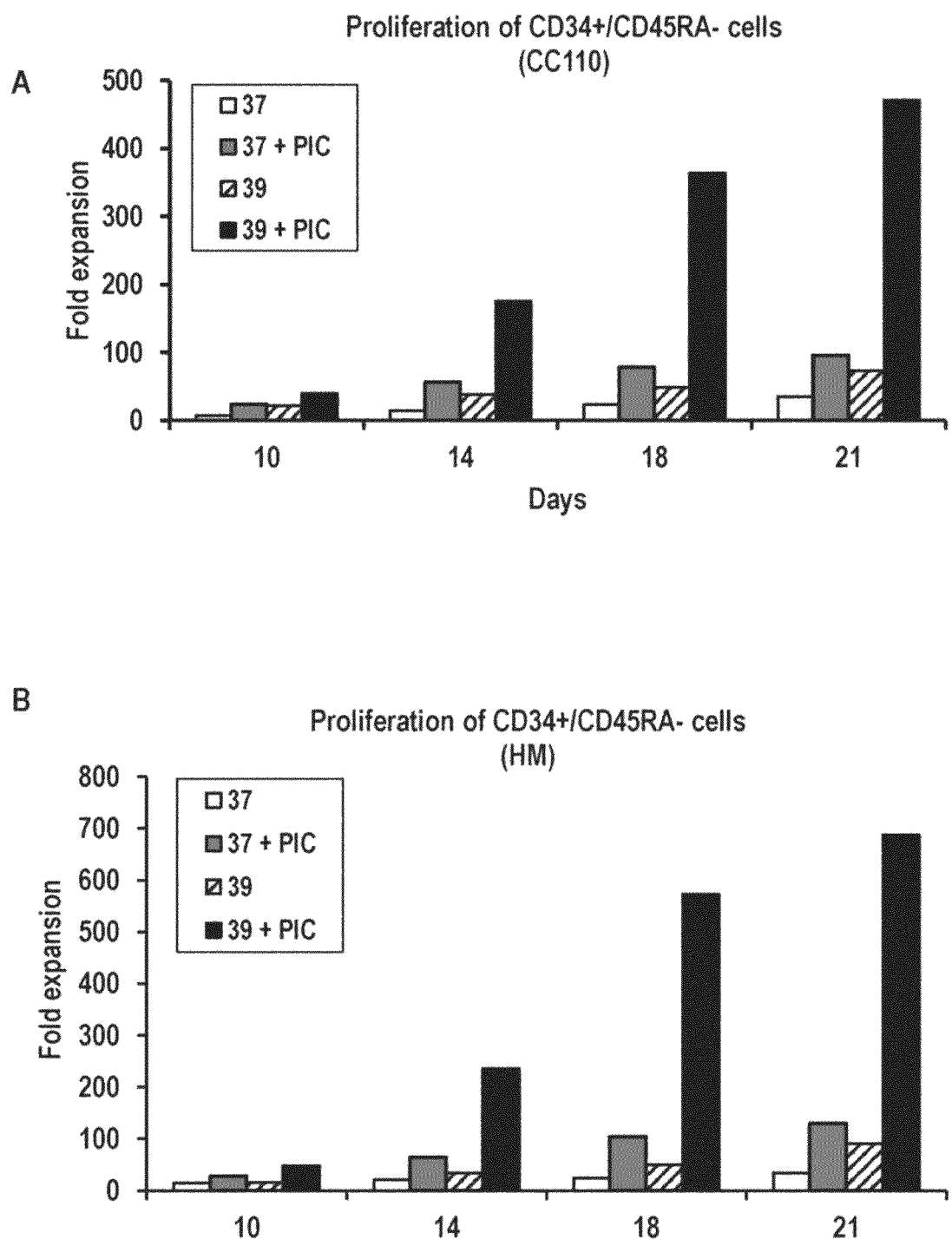
FIG. 15 shows the fold-expansion of cord blood-derived CD34+/CD45RA− (long-term hematopoietic stem cells; LT-HSGs) cells cultured in medium supplemented with either the CC110 cytokine cocktail (FIG. 15A) or the home-made (HM) cytokine cocktail (FIG. 15B). The cells were cultured in the presence ("39") or absence ("37") of mild hyperthermia and/or the presence or absence of PIC.

FIG. 15 shows the fold-expansion of CB CD34+/CD45RA− (long-term hematopoietic stem cells; LT-HSCs) cells cultured in StemSpan™ ACF medium supplemented with either the CC110 cytokine cocktail (FIG. 15A) or the home-made (HM) cytokine cocktail (FIG. 15B).

Table 3 shows the percentages of each of the indicated HSC subpopulations after culture of CB CD34+ cells in StemSpan™ ACF medium supplemented with either the home-made (HM) or CC110 cytokine cocktail for 14 days.

TABLE 3

Phenotypic analysis of CD34+ cells cultured in StemSpan ™ ACF medium supplemented with either the HM or CC110 cytokine cocktail

| Cytokine cocktail | Condition | Percentages of each of the indicated phenotypes ||||||
|---|---|---|---|---|---|---|---|
| | | CD34+ | CD45RA− | CD38− | CD34+/CD45RA− | CD34+/CD38− | CD34+/CD38−/CD45RA−/ |
| HM | 37° C. | 15.24 | 42.8 | 15.6 | 4.5 | 7.9 | 1.97 |
| | 37° C. + PIC | 51.5 | 53.4 | 12.05 | 22.4 | 32.4 | 14.7 |
| | 39° C. | 23.1 | 43.1 | 15.1 | 7.9 | 10.4 | 3.13 |
| | 39° C. + PIC | 40.95 | 35.2 | 12 | 24.8 | 22.9 | 15.7 |
| CC110 | 37° C. | 18.5 | 49 | 18.8 | 6.5 | 9.25 | 2.69 |
| | 37° C. + PIC | 48.9 | 59.2 | 14.8 | 16.36 | 30.3 | 10 |
| | 39° C. | 23 | 50.15 | 16.3 | 7.9 | 10.4 | 3.43 |
| | 39° C. + PIC | 43.7 | 40.85 | 14.45 | 23.05 | 24.2 | 14.1 |

Example 11

Effect of Different Basal Media and Cytokine Cocktails on Expansion of CD34+ Cells (HSCs) and CD34+/CD45RA− Cells (LT-HSCs) Under Mild Hyperthermia and PIC The results presented in this example show that synergistic expansion of CB CD34+ HSCs and CD34+/CD45RA− LT-HSCs under mild hyperthermia (39° C.) and PIC can be obtained using different commercially available media and different cytokine cocktails.

Human CB CD34+-enriched cells were obtained from human cord blood (CB) as described in Example 6.1, and were cultured in conditions favoring their self-renewal as generally described in Example 6.4, in the presence or absence of mild hyperthermia (39° C.) and/or the presence or absence of the pyrimidoindole compound PIC (see Example 2). Cellular counts and viability were determined as described in Example 6.5.

Figure 16:
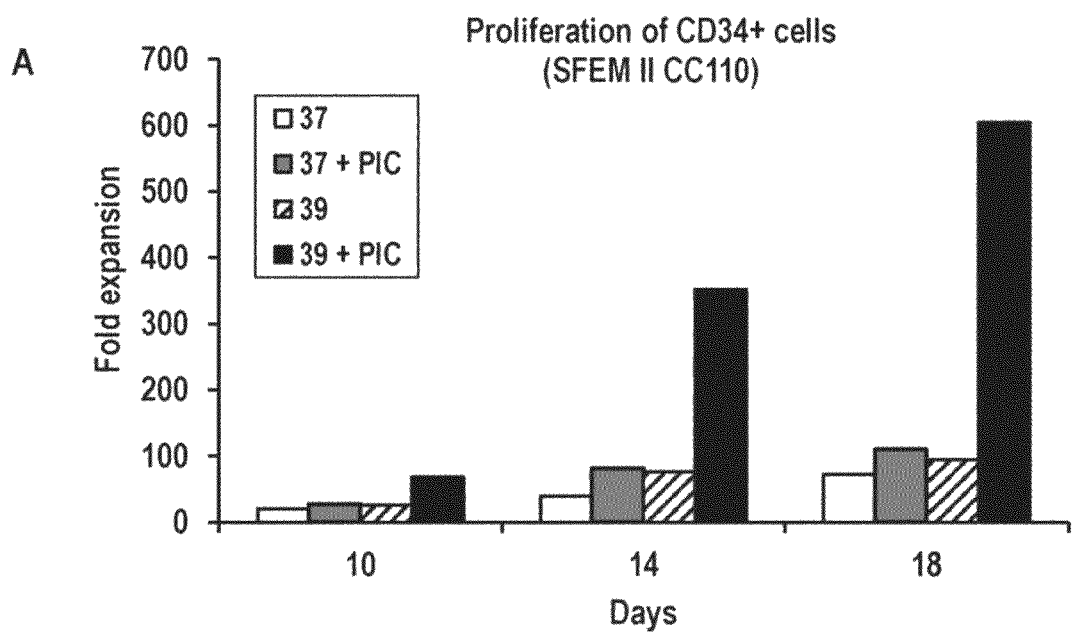
FIG. 16 shows the fold-expansion of cord blood-derived CD34+ cells (hematopoietic stem cells) cultured in StemSpan™ SFEM medium supplemented with either the CC110 cytokine cocktail (FIG. 16A) or the home-made (HM) cytokine cocktail (FIG. 16B). The cells were cultured in the presence ("39") or absence ("37") of mild hyperthermia and/or the presence or absence of PIC.
Figure 16:
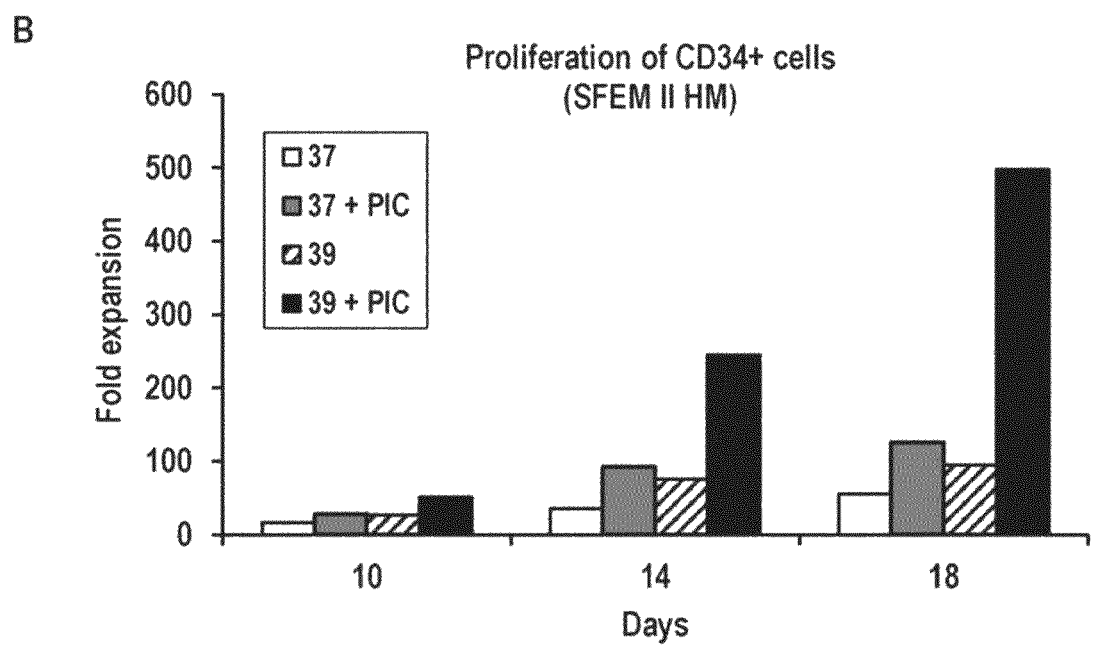

FIG. 16 shows the fold-expansion of CB CD34+ cells (hematopoietic stem cells) cultured in StemSpan™ SFEM medium supplemented with either the CC110 cytokine cocktail (FIG. 16A) or the home-made (HM) cytokine cocktail (FIG. 16B).

Figure 17:
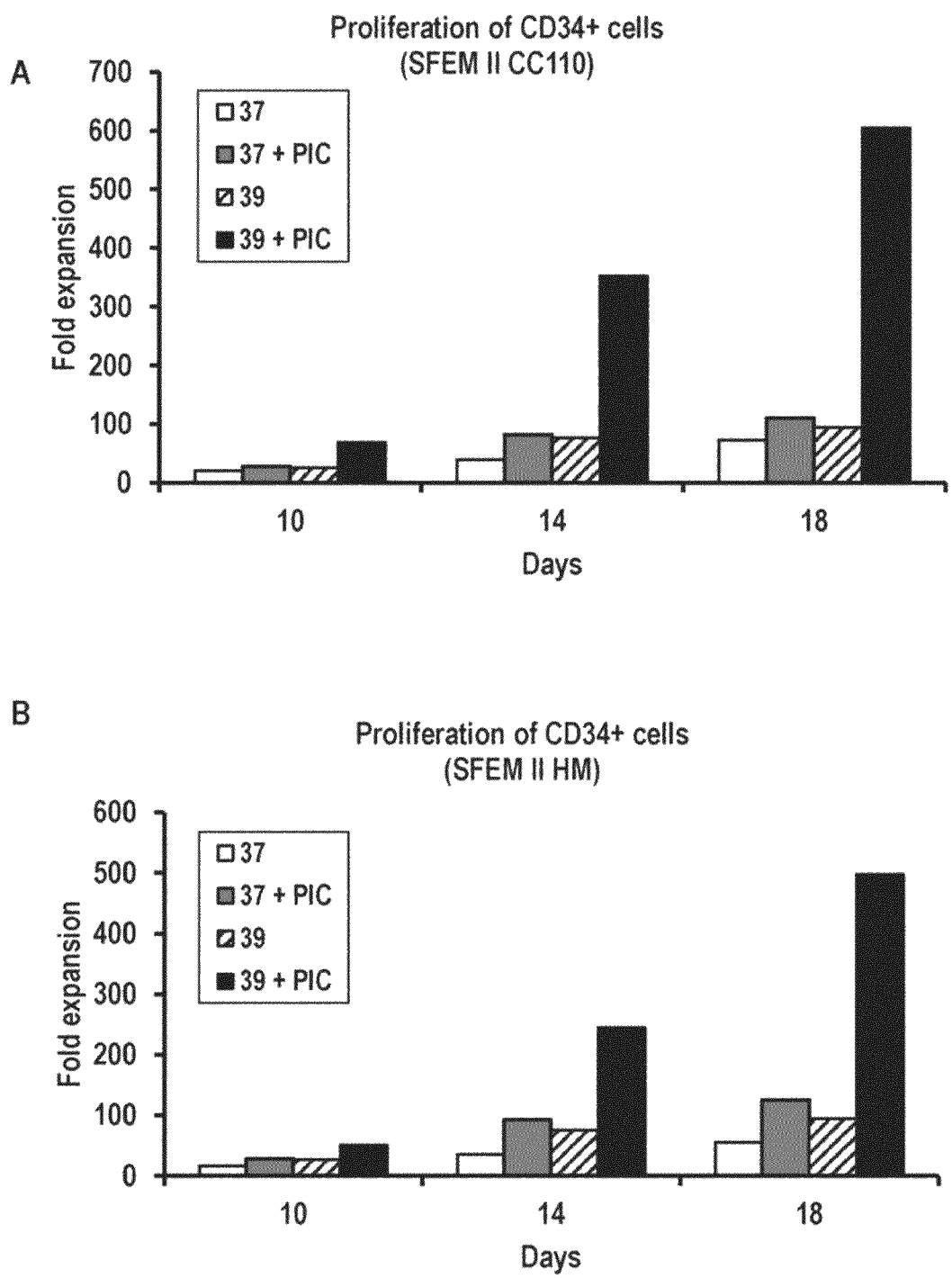
FIG. 17 shows the fold-expansion of cord blood-derived CD34+ cells (hematopoietic stem cells) cultured in StemSpan™ SFEM II medium supplemented with either the CC110 cytokine cocktail (FIG. 17A) or the home-made (HM) cytokine cocktail (FIG. 17B). The cells were cultured in the presence ("39") or absence ("37") of mild hyperthermia and/or the presence or absence of PIC.

FIG. 17 shows the fold-expansion of CB CD34+ cells (hematopoietic stem cells) cultured in StemSpan™ SFEM II medium supplemented with either the CC110 cytokine cocktail (FIG. 17A) or the home-made (HM) cytokine cocktail (FIG. 17B).

Figure 18:
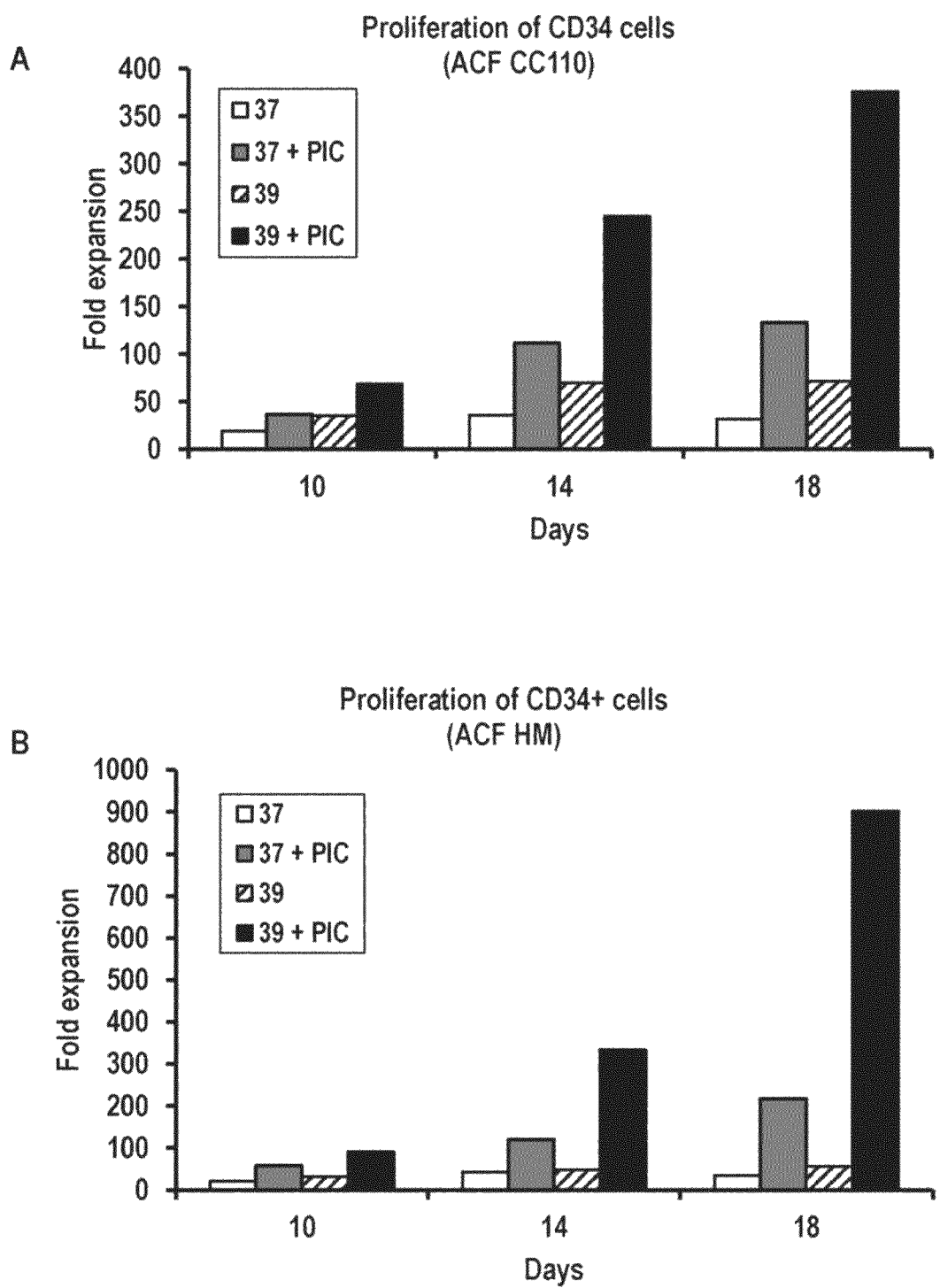
FIG. 18 shows the fold-expansion of cord blood-derived CD34+ cells (hematopoietic stem cells) cultured in StemSpan™ ACF medium supplemented with either the CC110 cytokine cocktail (FIG. 18A) or the home-made (HM) cytokine cocktail (FIG. 18B). The cells were cultured in the presence ("39") or absence ("37") of mild hyperthermia and/or the presence or absence of PIC.
Figure 18:
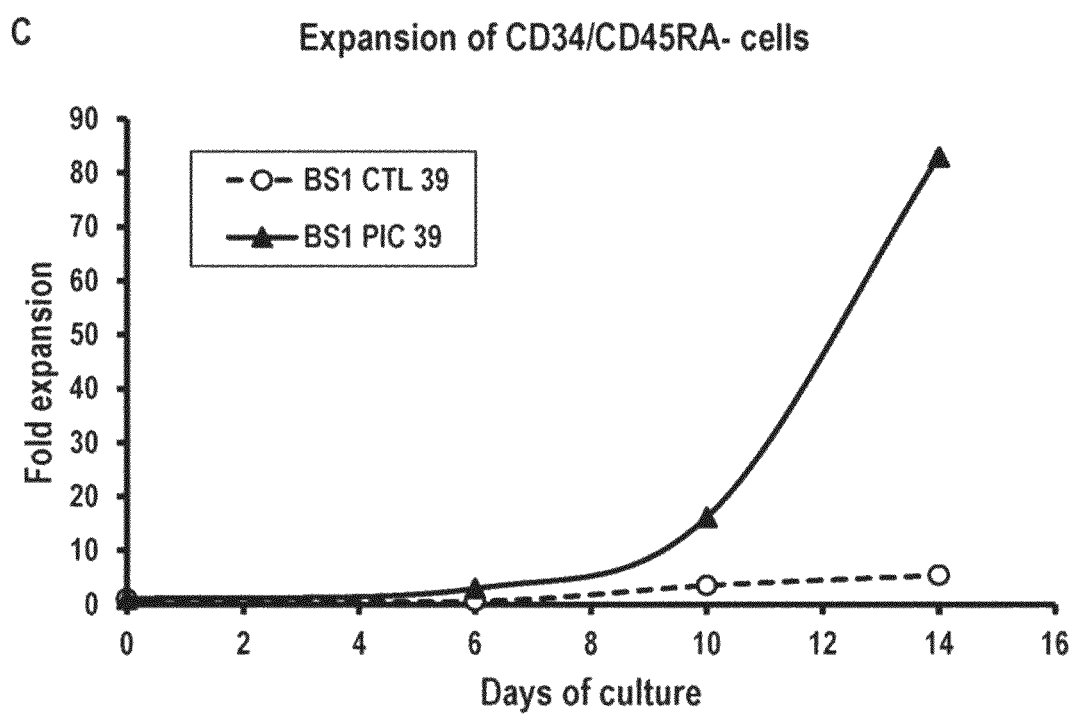

FIG. 18 shows the fold-expansion of CB CD34+ cells (hematopoietic stem cells) cultured in StemSpan™ ACF medium supplemented with either the CC110 cytokine cocktail (FIG. 18A) or the home-made (HM) cytokine cocktail (FIG. 18B). FIG. 18C shows the fold-expansion of CB CD34+/CD45RA− cells (long-term hematopoietic stem cells; LT-HSC) cultured in StemSpan™ SFEM medium supplemented with the BS1 cytokine cocktail under mild hyperthermia and in the presence ("39") or absence ("CTL") of PIC.

Table 4 shows the fold expansion of long-term hematopoietic stem cells (LT-HSCs) (CD34+/CD45RA−) from CB CD34+ cells cultured in various basal media using the CC110 or the home-made (HM) cytokine cocktail.

TABLE 4

Expansion of CD34+/CD45RA− cells (LT-HSCs) cultured in various basal media and cytokine cocktails

| Medium + cytokine cocktail | Condition | Fold expansion on the indicated days of culture | | | |
|---|---|---|---|---|---|
| | | Day 7 | Day 10 | Day 14 | Day 18 |
| SFEM + CC110 | 37° C. | 5.65 | 8.6 | 11.3 | 17.9 |
| | 37° C. + PIC | 4.14 | 6.7 | 14.2 | 27.1 |
| | 39° C. | 5.06 | 9.2 | 18.6 | 26.9 |
| | 39° C. + PIC | 7.01 | 19.8 | 67.8 | 129.4 |
| SFEM + HM | 37° C. | 4.35 | 8.8 | 8.8 | 13.8 |
| | 37° C. + PIC | 4.46 | 13.0 | 16.2 | 24.8 |
| | 39° C. | 6.44 | 11.5 | 16.9 | 24.8 |
| | 39° C. + PIC | 6.12 | 19.3 | 53.7 | 122.3 |
| SFEM II + CC110 | 37° C. | 6.38 | 6.8 | 7.7 | 22.1 |
| | 37° C. + PIC | 5.52 | 10.3 | 15.0 | 24.3 |
| | 39° C. | 6.93 | 9.2 | 14.6 | 31.9 |
| | 39° C. + PIC | 9.45 | 35.4 | 139.8 | 237.6 |
| SFEM II + HM | 37° C. | 4.57 | 6.0 | 27.7 | 18.8 |
| | 37° C. + PIC | 4.18 | 9.7 | 18.3 | 31.7 |
| | 39° C. | 7.28 | 9.5 | 63.3 | 29.8 |
| | 39° C. + PIC | 6.97 | 25.9 | 99.6 | 208.3 |
| ACF + CC110 | 37° C. | 3.99 | 5.9 | 8.6 | 15.4 |
| | 37° C. + PIC | 6.56 | 13.4 | 25.9 | 47.6 |
| | 39° C. | 4.96 | 10.0 | 18.0 | 33.1 |
| | 39° C. + PIC | 9.16 | 34.8 | 104.8 | 191.5 |
| ACF + HM | 37° C. | 4.38 | 6.2 | 11.9 | 17.1 |
| | 37° C. + PIC | 6.51 | 28.8 | 20.6 | 43.8 |
| | 39° C. | 4.43 | 8.7 | 10.8 | 21.5 |
| | 39° C. + PIC | 10.64 | 34.0 | 131.6 | 330.4 |

Table 5 shows the percentages of each of the indicated HSC subpopulations derived from CB CD34+ cells cultured for 14 days in various basal media (SFEM, SFEM II, or StemSpan ACF (ACF)) medium supplemented with the CC110 or home-made (HM) cytokine cocktail.

TABLE 5

Phenotypic analysis of CD34+ cells cultured in different basal media and in different cytokine cocktails

| Medium + cytokine cocktail | Condition | Percentages of each of the indicated phenotypes | | |
|---|---|---|---|---|
| | | CD34+ | CD45RA− | CD34+/CD45RA− |
| SFEM + CC110 | 37° C. | 18.6 | 66.99 | 4.41 |
| | 37° C. + PIC | 42.68 | 78.72 | 6.96 |
| | 39° C. | 18.94 | 58.78 | 4.72 |
| | 39° C. + PIC | 45.36 | 70.13 | 12.23 |
| SFEM + HM | 37° C. | 14.67 | 63.1 | 3.68 |
| | 37° C. + PIC | 37.4 | 75.74 | 6.66 |
| | 39° C. | 16.59 | 57.67 | 4.16 |
| | 39° C. + PIC | 41.95 | 69.88 | 12.39 |
| SFEM II + CC110 | 37° C. | 9.65 | 59.53 | 1.9 |
| | 37° C. + PIC | 33.38 | 77.73 | 6.09 |
| | 39° C. | 12.64 | 55.23 | 2.41 |
| | 39° C. + PIC | 37.9 | 63.9 | 15.03 |
| SFEM II + HM | 37° C. | 11.55 | 60.78 | 9.08 |
| | 37° C. + PIC | 30.82 | 77.27 | 6.11 |
| | 39° C. | 12.4 | 56.26 | 10.48 |
| | 39° C. + PIC | 37.56 | 63.45 | 15.27 |
| ACF + CC110 | 37° C. | 15.37 | 57.36 | 3.7 |
| | 37° C. + PIC | 50.98 | 76.09 | 11.83 |
| | 39° C. | 19.94 | 59.6 | 5.14 |
| | 39° C. + PIC | 43.73 | 59.72 | 18.73 |
| ACF + HM | 37° C. | 17.39 | 59.16 | 4.84 |
| | 37° C. + PIC | 44.62 | 77.44 | 7.67 |
| | 39° C. | 17.13 | 59.92 | 3.9 |
| | 39° C. + PIC | 44.82 | 59.67 | 17.68 |

FIG. 18C shows the fold-expansion of CB CD34+/CD45RA− cells (long-term hematopoietic stem cells; LT-HSC) cultured in StemSpan™ SFEM medium supplemented with the BS1 cytokine cocktail. These results show that a cell culture medium known for promoting expansion of megakaryocytic progenitor cells (CD34+/CD41+), also enables expansion of self-renewing LT-HSCs.

Example 12

Effect of the Combined Use of Mild Hyperthermia and PIC2 or PIC on Expansion of CD34+ Cells (HSCs), CD34+/CD45RA− Cells (LT-HSCs), and CD34+/CD38-/CD45RA− Cells Human CB CD34+-enriched cells were obtained from human cord blood (CB) as described in Example 6.1, and were cultured in conditions favoring their self-renewal as generally described in Example 6.4 in StemSpan™ ACF medium supplemented with the home-made (HM) cytokine cocktail, in the presence or absence of mild hyperthermia (39° C.) and/or the presence or absence of the pyrimidoindole compound PIC2 (see Example 7.4). Cellular counts and viability were determined as described in Example 6.5.

Figure 19:
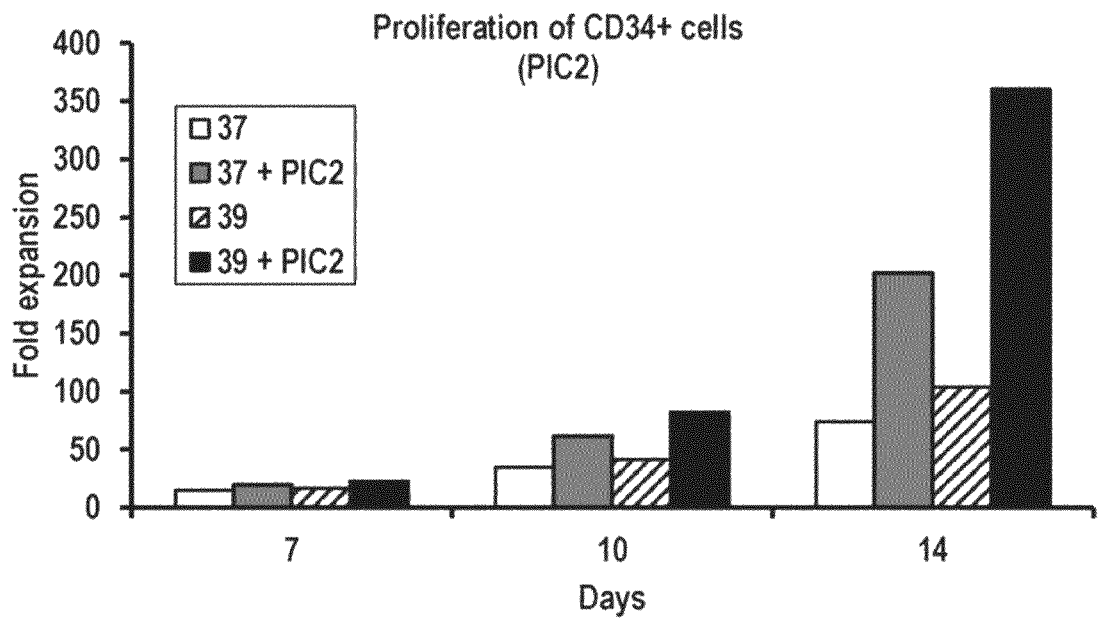
FIGS. 19, 20 and 21 show the fold-expansion of CD34+ cells (hematopoietic stem cells), CD34+/CD45RA− cells (LT-HSGs), and CD34+/CD38−/CD45RA− cells, respectively, after 7, 10, and 14 days in culture in the presence ("39") or absence ("37") of mild hyperthermia and/or the presence or absence of PIC2.
Figure 20:
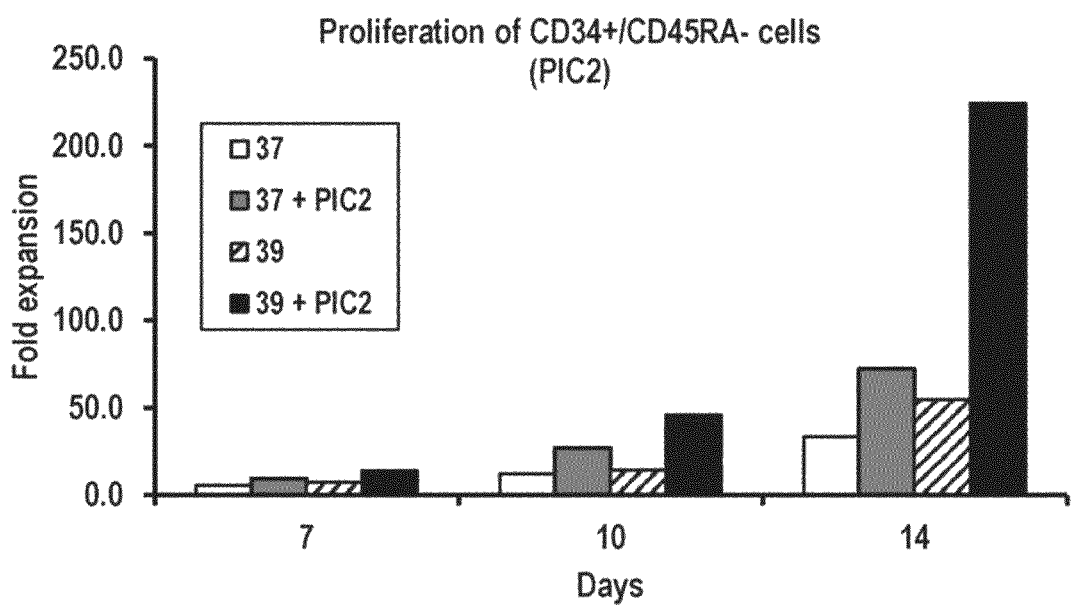
Figure 21:
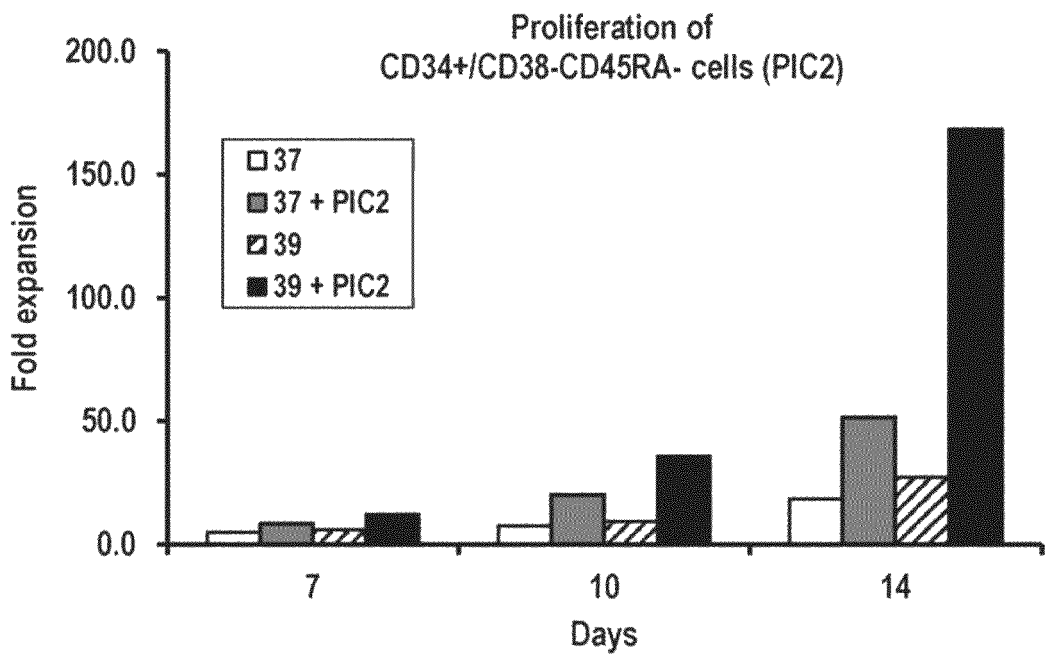

FIGS. 19, 20 and 21 show the fold-expansion of CD34+ cells (hematopoietic stem cells), CD34+/CD45RA− cells (LT-HSCs), and CD34+/CD38−/CD45RA− cells (Majeti et al., 2007), respectively, after 7, 10, and 14 days in culture.

Figure 22:
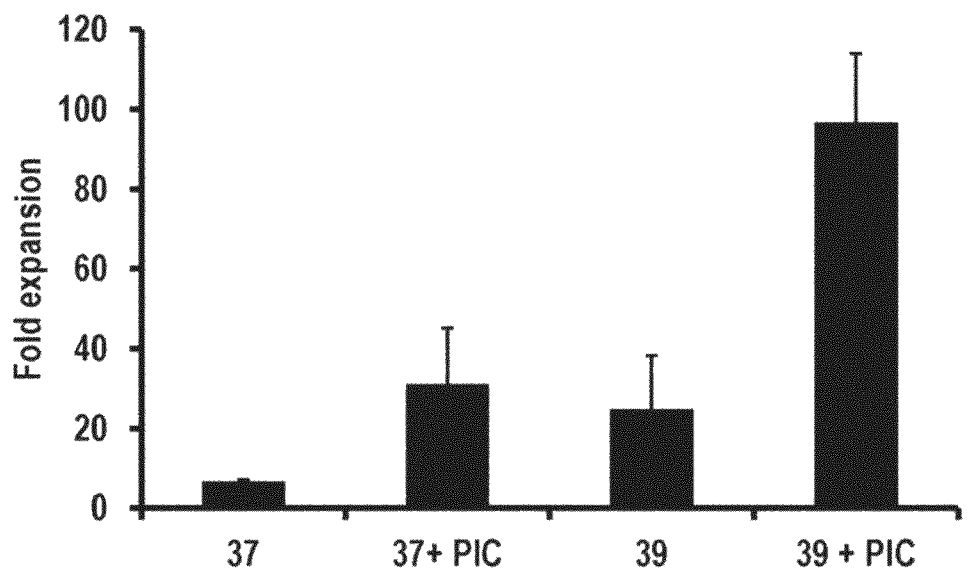
FIG. 22 shows the fold-expansion of CD34+/CD38−/CD45RA− cells after 14 days of culture under mild hyperthermia (39° C.) and PIC.

FIG. 22 shows the fold-expansion of CD34+/CD38−/CD45RA− cells after 14 days of culture under mild hyperthermia (39° C.) and PIC on the expansion of CB CD34+/CD38−/CD45RA− cells cultured for 14 days in StemSpan™ ACF medium supplemented with the home-made (HM) cytokine cocktail. Data represent means of four independent experiments.

Example 13

Effect of the Combined Use of Mild Hyperthermia and PIC on the Expansion of Mobilized Peripheral Blood (mPB) CD34+(HSCs), CD34+/CD45RA− (LT-HSCs), and CD34+/CD38−/CD45RA− Cells Human G-CSF-mobilized peripheral blood CD34+-enriched cells were obtained as described in Example 6.1, and were cultured in conditions favoring their self-renewal as generally described in Example 6.4 in StemSpan™ ACF medium supplemented with the home-made (HM) cytokine cocktail, in the presence or absence of mild hyperthermia (39° C.) and/or the presence or absence of the pyrimidoindole compound PIC (see Example 2). Cellular counts and viability were determined as described in Example 6.5.

Figure 23:
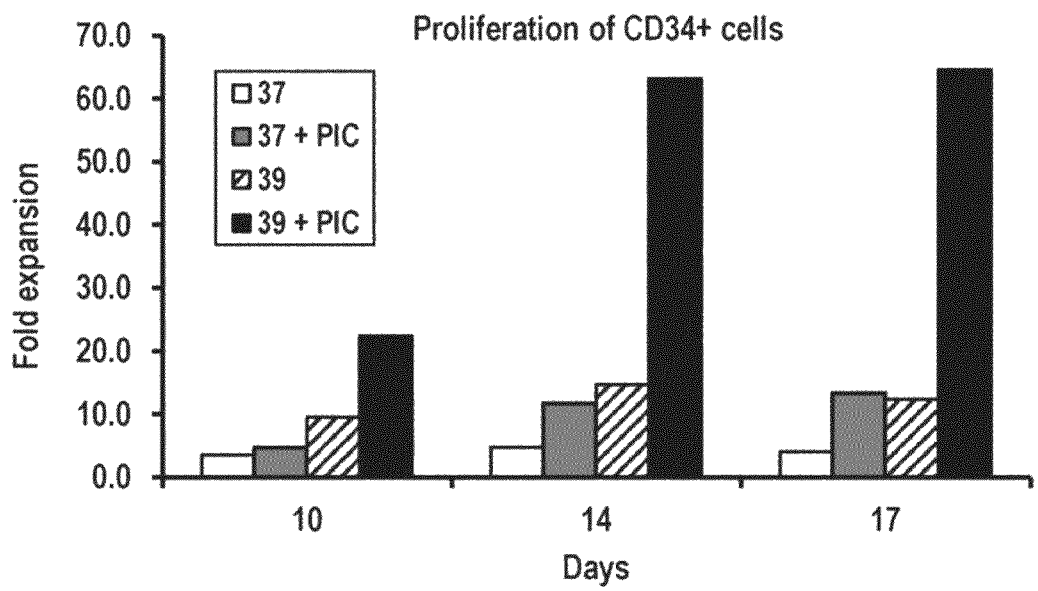
FIGS. 23, 24 and 25 show the fold-expansion of mobilized peripheral blood-derived CD34+ cells (hematopoietic stem cells), CD34+/CD45RA− cells (LT-HSGs), and CD34+/CD38−/CD45RA− cells, respectively, after 10, 14, and 17 days in culture in the presence ("39") or absence ("37") of mild hyperthermia and/or the presence or absence of PIC.
Figure 24:
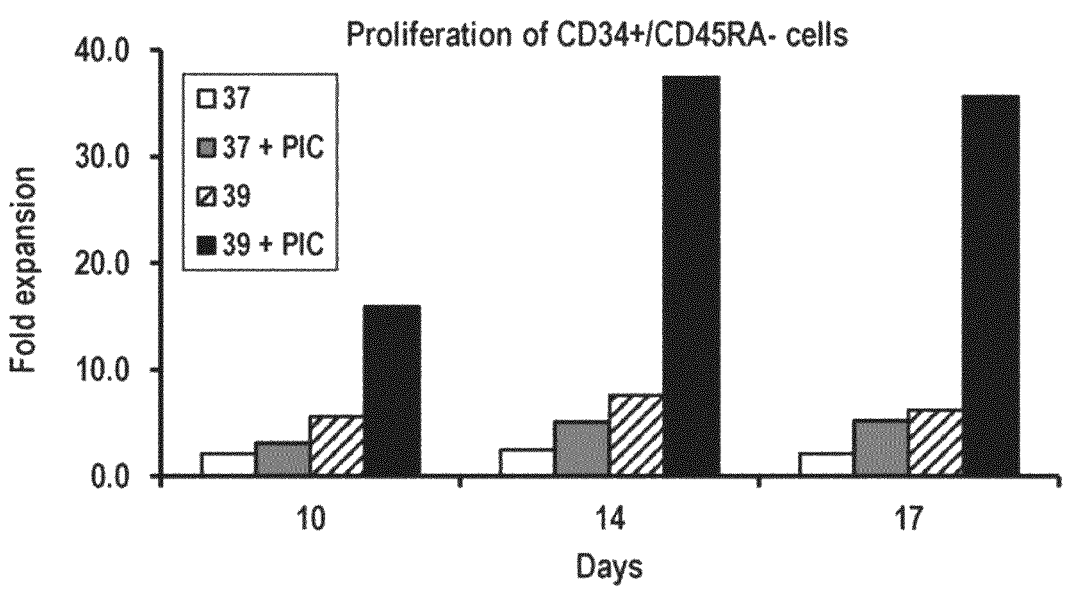
Figure 25:
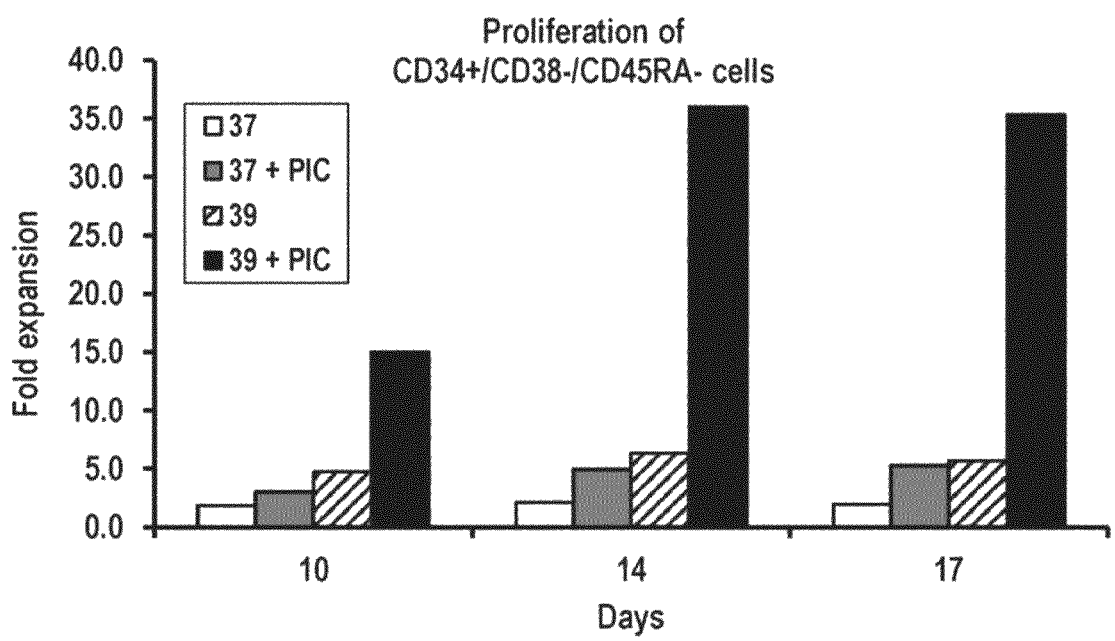

FIGS. 23, 24 and 25 show the fold-expansion of CD34+ cells (hematopoietic stem cells), CD34+/CD45RA− cells (LT-HSCs), and CD34+/CD38−/CD45RA− cells, respectively, after 10, 14, and 17 days in culture.

Example 14

Effect of the Combined Use of Mild Hyperthermia and PIC on the Expansion of Bone Marrow CD34+(HSCs), CD34+/CD45RA− (LT-HSCs), and CD34+/CD38-CD45RA− Cells Human bone marrow (BM) CD34+-enriched cells were obtained as described in Example 6.1, and were cultured in conditions favoring their self-renewal as generally described in Example 6.4 in StemSpan™ ACF medium supplemented with the home-made (HM) cytokine cocktail, in the presence or absence of mild hyperthermia (39° C.) and/or the presence or absence of the pyrimidoindole compound PIC (see Example 2). Cellular counts and viability were determined as described in Example 6.5.

Figure 26:
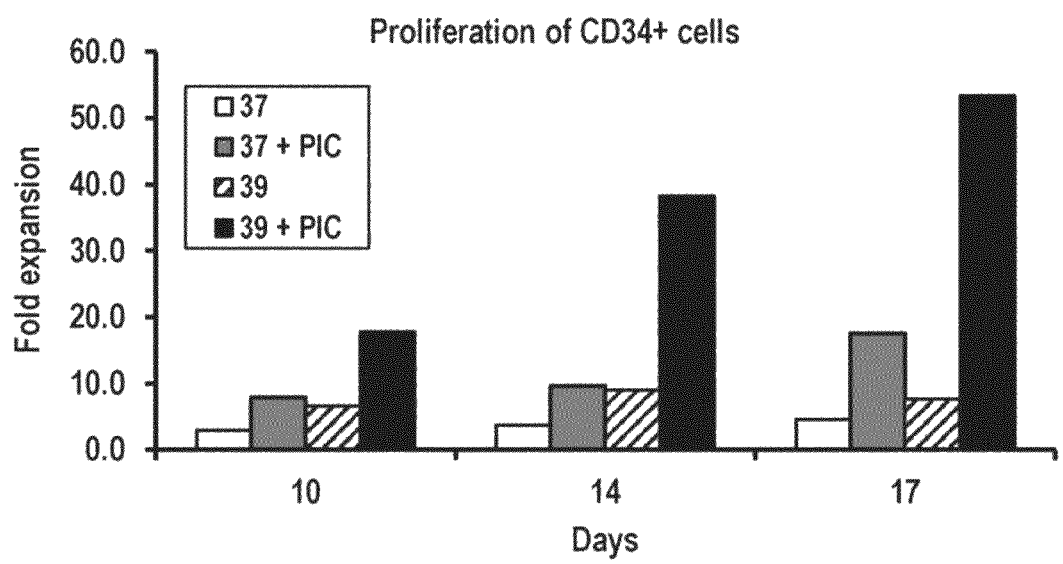
FIGS. 26, 27 and 28 show the fold-expansion of human bone marrow-derived CD34+ cells (hematopoietic stem cells), CD34+/CD45RA− cells (LT-HSGs), and CD34+/CD38−/CD45RA− cells, respectively, after 10, 14, and 17 days in culture in the presence ("39") or absence ("37") of mild hyperthermia and/or the presence or absence of PIC.
Figure 27:
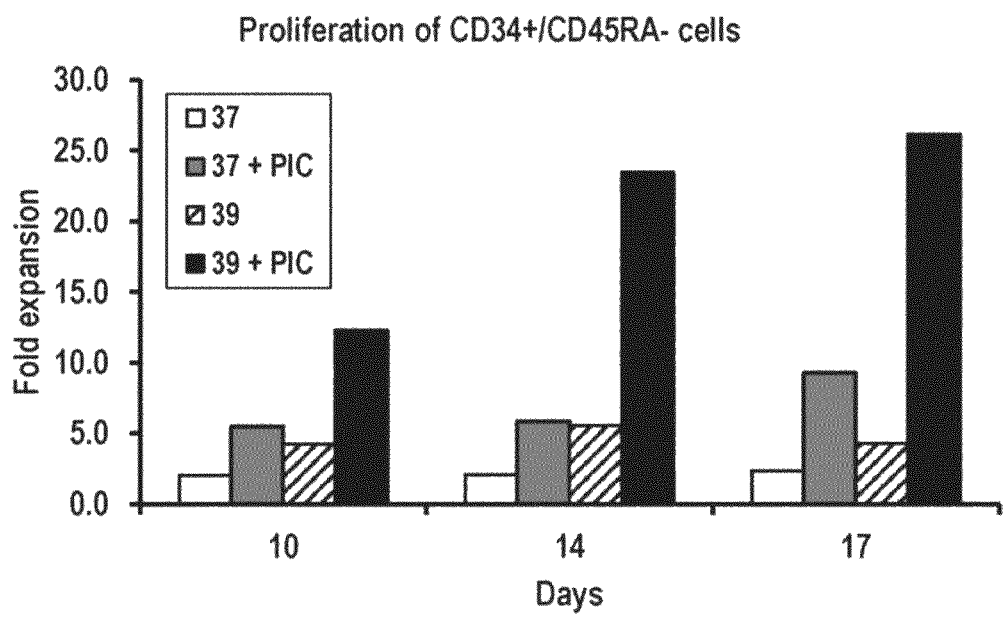
Figure 28:
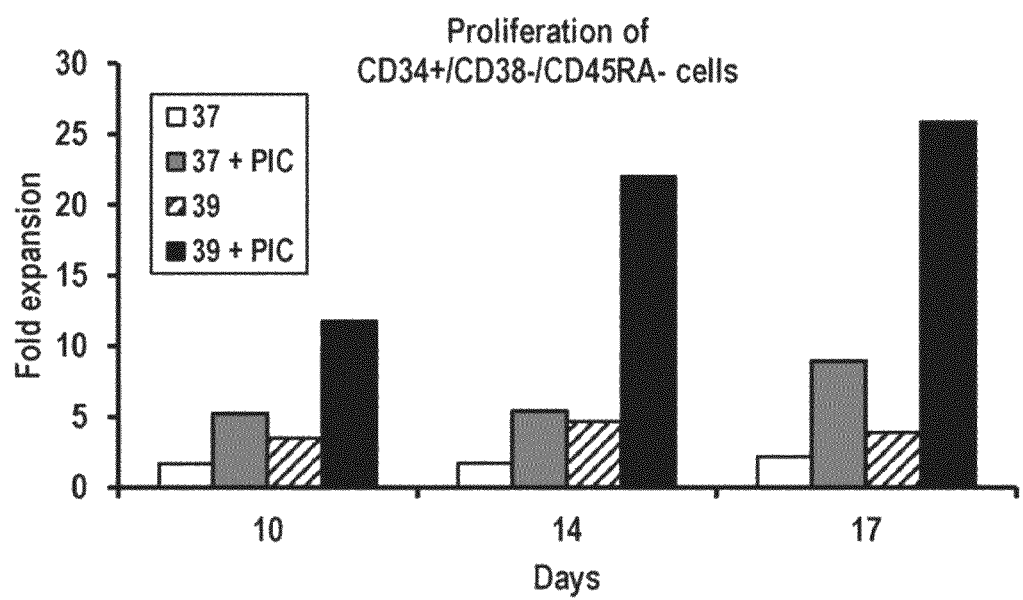

FIGS. 26, 27 and 28 show the fold-expansion of CD34+ cells (hematopoietic stem cells), CD34+/CD45RA− cells (LT-HSCs), and CD34+/CD38−/CD45RA− cells, respectively, after 10, 14, and 17 days in culture.

Example 15

Effect of the Combined Use of Mild Hyperthermia and PIC on the Expansion of CB CD34+/ALDH$^{Bright}$ Cells Human CB CD34+-enriched cells were obtained from human cord blood (CB) as described in Example 6.1, and were cultured in conditions favoring their self-renewal as generally described in Example 6.4 in StemSpan™ ACF medium supplemented with the home-made (HM) cytokine cocktail, in the presence or absence of mild hyperthermia (39° C.) and/or the presence or absence of the pyrimidoindole compound PIC (see Example 2). Cellular counts and viability were determined as described in Example 6.5.

Figure 29:
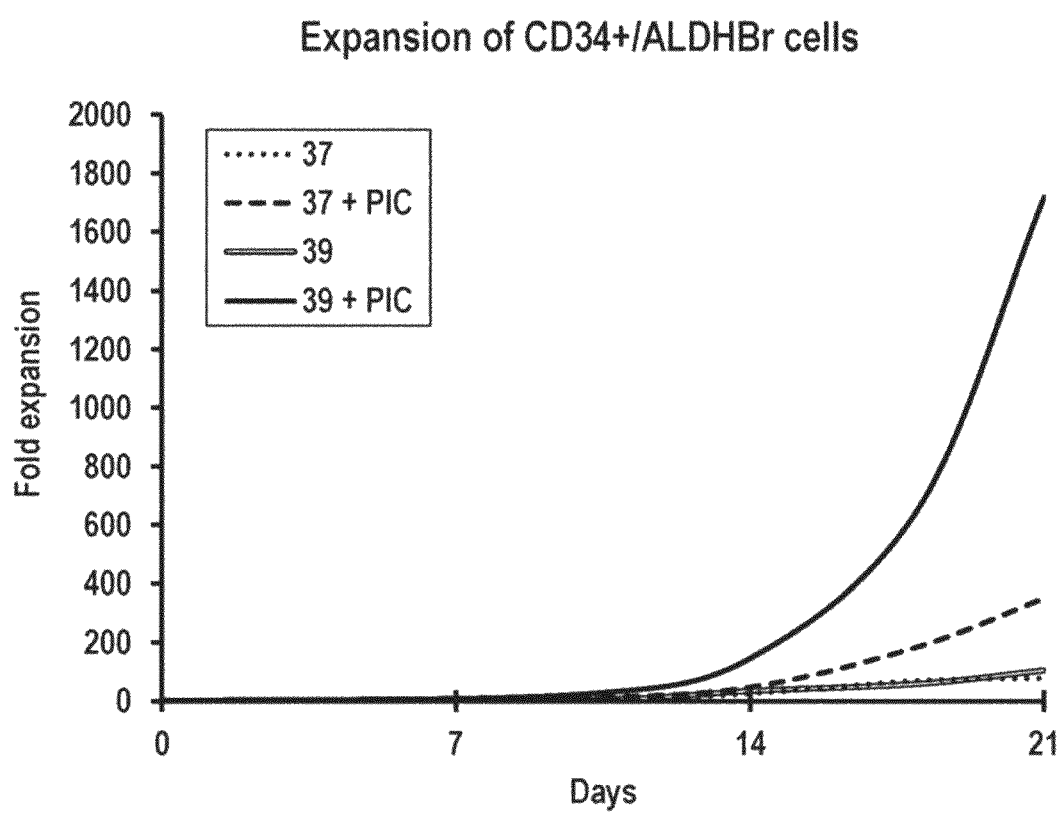
FIG. 29 shows the fold-expansion of CD34+/ALDH$^{Bright}$ cells over 21 days in culture in the presence ("39") or absence ("37") of mild hyperthermia and/or the presence or absence of PIC.

FIG. 29 shows the fold-expansion of CD34+/ALDH$^{Bright}$ cells after 21 days of culture. These results indicate that the combined use of mild hyperthermia and PIC results in a synergistic expansion of this subpopulation of HSCs.

Example 16

Transplantation and Engraftment in Immunodeficient Mice of Human CB CD34+ Cells (HSCs) Expanded In Vitro Under Mild Hyperthermia and PIC Human CB CD34+-enriched cells were obtained from human cord blood (CB) as described in Example 6.1, and were cultured in conditions favoring their self-renewal as generally described in Example 6.4 in StemSpan™ ACF medium supplemented with the home-made (HM) cytokine cocktail in the presence of mild hyperthermia (39° C.) and the pyrimidoindole compound PIC (see Example 2). Fresh CB CD34+ cells, or CB CD34+ cells that had been expanded for 12 days, were transplanted into immunodeficient mice as described in Example 6.8.

An increase in the percentage of human CD45+ cells in the bone marrow of mice transplanted with the in vitro expanded CB CD34+ cells was observed, as compared to the mice transplanted with PBS alone, indicating successful engraftment (data not shown).

REFERENCES

Cortin et al., (2005). Efficient in vitro megakaryocyte maturation using cytokine cocktails optimized by statistical experimental design. *Exp Hematol* 33 (10): 1182-1191.

Fares et al., (2014). Cord blood expansion. Pyrimidoindole derivatives are agonists of human hematopoietic stem cell self-renewal. *Science* 345 (6203): 1509-1512.

Majeti et al., (2007). Identification of a hierarchy of multipotent hematopoietic progenitors in human cord blood. *Cell Stem Cell* 1 (6): 635-645.

Proulx et al., (2004). Increased megakaryopoiesis in cultures of CD34-enriched cord blood cells maintained at 39 degrees C. *Biotechnol Bioeng* 88 (06): 675-680.

Robert et al., (2011). Glycoprotein Ibα receptor instability is associated with loss of quality in platelets produced in culture. *Stem Cells and Development* 20 (03): 379-390.

The invention claimed is:

1. An in vitro method for the preferential expansion of hematopoietic stem cells (HSCs) and differentiation to megakaryocytic progenitor cells, said method comprising propagating the HSCs in a cell culture medium comprising a pyrimido[4,5-b] indole derivative which is an agonist of hematopoietic stem cell expansion under conditions of mild hyperthermia for a sufficient period of time to obtain an in vitro cell population comprising at least 40% of CD34+/CD41+ megakaryocytic progenitor cells, wherein said cell culture medium is a medium promoting differentiation of HSCs towards a megakaryocytic lineage, and said mild hyperthermia is an incubation temperature of between 38° C. and 40° C.

2. The method of claim 1, wherein:
(i) said HSCs are CD34+ hematopoietic stem cells; or
(ii) said HSCs are from: umbilical cord blood; bone marrow; peripheral blood; induced pluripotent stem cells; embryonic stem cells; transdifferentiated from differentiated cells of non-hematopoietic origin; genetically modified hematopoietic stem cells; immortalized hematopoietic stem cells; other sources of pluripotent or multipotent cells; or any combination thereof or
(iii) both (i) and (ii).

3. The method of claim 2, wherein said HSCs are from mobilized peripheral blood cells, or are from residual cells following leukoreduction, deleukocytation, or other blood purification or processing of peripheral blood, or are from both mobilized peripheral blood cells and residual cells.

4. The method of claim 2, wherein said HSCs are from unmobilized peripheral blood cells.

5. The method of claim 1, wherein said sufficient period of time is at least 6 days.

6. The method of claim 5, wherein said sufficient period of time is at least 7 days.

7. The method of claim 6, wherein said sufficient period of time is at least 8 days.

8. The method of claim 7, wherein said sufficient period of time is about 9-21 days.

9. The method of claim 1, wherein said incubation temperature is 39° C.

10. The method of claim 1, wherein said pyrimido[4,5-b]indole derivative is:
(1) (1r,4r)-N1-(2-benzyl-7-(2-methyl-2H-tetrazol-5-yl)-9H-pyrimido[4,5-b]indol-4yl)cyclohexane-1,4-diamine;
(2) methyl 4-(3-(piperidin-1-yl)propylamino)-9H-pyrimido[4,5-b]indole-7-carboxylate;
(3) methyl 4-(3-(piperidin-1-yl)propylamino)-9H-pyrimido[4,5-b]indole-7-carboxylate hydrochloride;
(4) a pharmaceutically acceptable salt, solvate, prodrug, or stereoisomer of any one of (1) to (3); or
(5) any combination of (1) to (4).

11. The method of claim 1, wherein said cell culture medium comprises: stem cell factor (SCF); thrombopoietin (TPO); human FMS-like tyrosine kinase 3 ligand (FLT3); IL-6; IL-9; or any combination thereof.

12. The method of claim 1, further comprising: removing said pyrimido[4,5-b]indole derivative and continuing to culture said in vitro cell population comprising at least 40% of CD34+/CD41+ megakaryocytic progenitor cells at an incubation temperature between 38° C. and 40° C.

13. The method of claim 1, wherein the method results in said in vitro cell population comprising at least about 45%, of said CD34+/CD41+ cells.

14. The method of claim 13, further comprising isolating the CD34+/CD41+ megakaryocytic progenitor cells.

15. The method of claim 13, wherein the method results in said in vitro expanded cell population comprising at least about 50% of said CD34+/CD41+ cells.

16. The method of claim 1, wherein said pyrimidoindole derivative agonist of hematopoietic stem cell expansion is: (1r,4r)-N1-(2-benzyl-7-(2-methyl-2H-tetrazol-5-yl)-9H-pyrimido[4,5-b]indol-4-yl)cyclohexane-1,4-diamine; or a pharmaceutically acceptable salt, solvate, prodrug, or stereoisomer thereof.

17. The method of claim 16, further comprising isolating the CD34+/CD41+ megakaryocytic progenitor cells.

18. The method of claim 1, wherein said pyrimidoindole derivative agonist of hematopoietic stem cell expansion is: methyl 4-(3-(piperidin-1-yl)propylamino)-9H-pyrimido[4,5-b]indole-7-carboxylate; methyl 4-(3-(piperidin-1-yl)propylamino)-9H-pyrimido[4,5-b]indole-7-carboxylate hydrochloride; or a pharmaceutically acceptable salt, solvate, prodrug, or stereoisomer thereof.

19. The method of claim 18, further comprising isolating the CD34+/CD41+ megakaryocytic progenitor cells.

20. The method of claim 1, further comprising isolating the CD34+/CD41+ megakaryocytic progenitor cells.

* * * * *